(12) United States Patent
Dahiyat et al.

(10) Patent No.: US 6,627,186 B1
(45) Date of Patent: Sep. 30, 2003

(54) NUCLEIC ACIDS AND PROTEIN VARIANTS OF HG-CSF WITH GRANULOPOIETIC ACTIVITY

(75) Inventors: Bassil I. Dahiyat, Los Angeles, CA (US); Peizhi Luo, Arcadia, CA (US)

(73) Assignee: Xencor, Monrovia, CA (US)

( * ) Notice: Subject to any disclaimer, the term of this patent is extended or adjusted under 35 U.S.C. 154(b) by 0 days.

(21) Appl. No.: 09/479,313

(22) Filed: Jan. 6, 2000

Related U.S. Application Data

(60) Provisional application No. 60/115,131, filed on Jan. 6, 1999, and provisional application No. 60/118,831, filed on Feb. 5, 1999.

(51) Int. Cl.[7] .................. A61K 38/19; C07K 14/535; C12N 1/21; C12N 5/10; C12N 15/27
(52) U.S. Cl. .................. 424/85.1; 514/2; 514/12; 435/69.1; 435/320.1; 435/252.3; 435/254.11; 435/325; 536/23.1; 536/23.5; 530/351; 530/350
(58) Field of Search .................. 530/350, 351, 530/399; 435/69.1, 325, 365.1, 320.1, 252.3, 254.11; 536/23.5, 23.1; 514/2, 8; 424/85.1

(56) References Cited

U.S. PATENT DOCUMENTS

| | | | |
|---|---|---|---|
| 4,810,643 A | 3/1989 | Souza | |
| 4,833,127 A | 5/1989 | Ono et al. | |
| 4,999,291 A | 3/1991 | Souza | |
| 5,214,132 A | 5/1993 | Kuga et al. | |
| 5,218,092 A * | 6/1993 | Sasaki et al. | |
| 5,362,853 A | 11/1994 | Kuga et al. | |
| 5,399,345 A * | 3/1995 | Schumacher et al. | |
| 5,416,195 A | 5/1995 | Camble et al. | |
| 5,580,755 A | 12/1996 | Souza | |
| 5,581,476 A | 12/1996 | Osslund | |
| 5,790,421 A | 8/1998 | Osslund | |
| 5,830,705 A | 11/1998 | Souza | |

FOREIGN PATENT DOCUMENTS

| | | |
|---|---|---|
| EP | 0 459 630 | 4/1991 |
| WO | 94/17185 | 8/1994 |
| WO | 98/47089 | 10/1998 |

OTHER PUBLICATIONS

Kuwabara et al. 1992, J. Pharamacobio–Dyn. vol. 15: pp. 121–129, Highly sensitive enzyme–linked immunosorbent assay for marograstim (KW–2228), a mutant of human granulocyte stimulating factor.*

Dahiyat et al., "Protein design automation," Protein Science, 5:895–903 (1996).

Kuga et al., "Mutagenesis of human granulocyte colony stimulating factor," Biochemical and Biophysical Research Communications, 159(1):103–111 (1989).

Luo et al., "Automated Design of Enhanced Granulopoietic Proteins," FASEB Journal, 13(7): a1431 (1999).

* cited by examiner

*Primary Examiner*—Elizabeth Kemmerer
(74) *Attorney, Agent, or Firm*—Dorsey & Whitney LLP; Robin M. Silva; Renee M. Kosslak

(57) ABSTRACT

The invention relates to novel granulopoietic activity (GPA) proteins and nucleic acids. The invention further relates to the use of the GPA proteins in the treatment of G-CSF related disorders.

27 Claims, 16 Drawing Sheets

TPLGPASSLPQSFLLKCLEQVRKIQGDGAALQEKLCATYKLCHPEELVLLGHSLGIPWA
PLSSCPSQALQLAGCLSQLHSGLFLYQGLLQALEGISPELGPTLDTLQLDVADFATTIW
QQMEELGMAPALQPTQGAMPAFASAFQRRAGGVLVASHLQSFLEVSYRVLRHLAQP hGCSF wild type ATGACTCCATTAGTTCAGTCTCCTCTGCCGGAAAGCTTCCTGCTGAAATCCAGGTGATGG
TGCTGCTCTGCAGGAAAAACTGTGCGCTACAAACTGTGCCATCCGGAAGAACTGGTTCTGCTGGGTCACTCCCTGGGTATCC
CGTGGGGCGCCGCTGAGCTCTGCCTGCCCAGCCTGCACAGCGGCCTTTCCTGTAC
CAGGGTCTGCTGCAAGCTCTGGAAGTTATCTCCCGAACTGGGTCCAGCTGGACACTCTGCAGCTGGACGTCGCGACTTCGC
TACCACCATCTGGCAGCAGATGGAAGAACTGGGTATGGCTCCAGCCGACCCAGGGTGCTATGCCGGCTTTCGCTTCCG
CTTTCCAGCCGTCGCGCCAGGTGGCGTTCCTAGCACCCTGCAGGGCTTCCTGGAAGTTTCCTACCGTGTTCTGCGTCACCTG
GCTCAGCCGTGA

FIG.—1

| | | | | | | | | | | | | | | | | | | |
|---|---|---|---|---|---|---|---|---|---|---|---|---|---|---|---|---|---|---|
| core3 | 17 95 | 21 99 | 24 103 | 28 106 | 31 110 | 35 113 | 41 114 | 47 117 | 54 140 | 56 151 | 75 152 | 78 153 | 82 154 | 85 157 | 88 160 | 89 161 | 92 168 | |
| core4 | 17 150 | 21 151 | 24 152 | 28 153 | 31 154 | 75 157 | 78 160 | 82 161 | 85 168 | 89 | 103 | 106 | 110 | 113 | 114 | 117 | 149 | |
| core4v | 17 152 | 21 153 | 24 154 | 28 157 | 31 160 | 75 161 | 78 167 | 82 168 | 85 | 89 | 103 | 106 | 110 | 113 | 114 | 117 | 151 | |
| bndry4_2 | 14 120 | 20 145 | 27 146 | 32 147 | 34 148 | 38 155 | 77 156 | 79 164 | 84 170 | 91 | 99 | 102 | 107 | 109 | 116 | | | |
| bndry4_core4 | 14 120 | 20 145 | 27 146 | 32 147 | 34 148 | 38 155 | 77 156 | 79 164 | 84 170 | 91 | 99 | 102 | 107 | 109 | 116 | | | |
| bndry4_AD | 14 | 20 | 27 | 32 | 34 | 38 | 145 | 146 | 147 | 148 | 155 | 156 | 164 | 170 | | | | |
| bndry4_AD_core4 | 14 | 20 | 27 | 32 | 34 | 38 | 145 | 146 | 147 | 148 | 155 | 156 | 164 | 170 | | | | |

*FIG._2*

G-CSF Designs - Optimal Sequences Selected by PDA*

|  | 1 | 10 | 20 | 30 | 40 | 50 | 60 |
|---|---|---|---|---|---|---|---|
| hGCSFwt | MTPLGPASSLPQSFLLKCLEQVRKIQGDGAALQEKLCATYKLCHPEELVLLGHSLGIPWAP |
| bndry4_2 |  |  | I | L | E | I I K |  |
| bndry4_core4 |  |  | I L L | EA | L E H |  |  |
| bndry4_AD |  |  | I L | E | I E H |  |  |
| bndry4_AD_core4 |  |  | I L L | EA | L E H |  |  |
| core4 |  |  | L | A |  |  |  |
| core4_V167A |  |  | L I | A |  |  |  |
| core3 |  |  | L | A | I |  |  |
| sm0 |  |  | L | A |  |  |  |
| fm2 |  |  | A | A |  |  |  |
| fm3 |  |  | A | A |  |  |  |
| fm4 |  |  | L | A |  |  |  |
| fm7 |  |  | L | A |  |  |  |

|  | 70 | 80 | 90 | 100 | 110 | 120 |
|---|---|---|---|---|---|---|
| hGCSFwt | LSSCPSQALQLAGCLSQLHSGLFLYQGLLQALEGISPELGPTLDTLQLDVADFATTIWQQ |
| bndry4_2 | L | F |  | V | I E I L |  |
| bndry4_core4 | FL | F | K | V I | I E I L |  |
| bndry4_AD | L | F |  | V | I E I L |  |
| bndry4_AD_core4 | FL | F | K | KV | I E I L |  |
| core4 |  | F |  | V |  H I L |  |
| core4_V167A |  | F |  | V |  H I L |  |
| core3 |  | F F F |  |  |  I L |  |
| sm0 |  |  |  |  |  |  |
| fm2 |  | F |  |  |  L L |  |
| fm3 |  | F |  |  |  |

```
                    130       140       150       160       170
hGCSFwt         MEELGMAPALQPTQGAMPAFASAFQRRAGGVLVASHLQSFLEVSYRVLRHLAQP
bndry4_2                                KED   IL    A
bndry4_core4                            KED I I IL  A     F
bndry4_AD                               KET   IL    A
bndry4_AD_core4                         KED I I IL  A     F
core4                                       I I     A     F
core4_V167A                                 I I  I  WF    AF
core3                                       I I           F
- - - - - - - - - - - - - - - - - - - - - - - - - - - - - - -
sm0
fm2                                         I I
fm3                                                       F
fm4                                         I I           F
fm7                                         I I           F
```

*Sequences shown below dotted lines were not obtained from PDA calculations but were derived by reverting some core4 or core3 mutant positions to wild type. Core4 mutant positions are indicated in bold. The sequence selected for Core4_V167A is not the ground state; Monte Carlo analysis shows the ground state with Phe instead of Trp for position 160, and Leu instead of Phe for position 161 (see Table 4).

FIG._3B

Core4 - Monte Carlo Analysis - Ground State and Allowed Amino Acids
and Their Number of Occurrences (For the Top 1000 Sequences)

| hG-CSF | Position | Ground State | | | | | | |
|---|---|---|---|---|---|---|---|---|
| CYS | 17 | LEU | 736 | ILE | 229 | | | |
| VAL | 21 | VAL | 687 | ILE | 287 | | | |
| ILE | 24 | VAL | 38 | ILE | 961 | | | |
| GLY | 28 | ALA | 747 | LEU | 172 | | | |
| LEU | 31 | VAL | 251 | LEU | 707 | | | |
| LEU | 75* | LEU | 999 | | | | | |
| LEU | 78 | PHE | 974 | | | | | |
| LEU | 82* | LEU | 974 | | | | | |
| TYR | 85 | PHE | 847 | TYR | 140 | | | |
| LEU | 89 | LEU | 628 | PHE | 321

Table 4. Core4v - Monte Carlo Analysis (Ground State and Allowed Amino Acids and Their Number of Occurrences (For the Top 1000 Sequences)

| hG-CSF | Position | Ground State | | | | | | | | |
|---|---|---|---|---|---|---|---|---|---|---|
| CYS | 17 | LEU | 697 | VAL | 51 | ILE | 251 | PHE | 17 | |
| VAL | 21 | VAL | 682 | VAL | 682 | ILE | 300 | | | |
| ILE | 24 | ILE | 938 | VAL | 61 | | | | | |
| GLY | 28 | ALA | 806 | LEU | 193 | | | | | |
| LEU | 31 | LEU | 694 | ALA | 1 | VAL | 257 | ILE | 47 | |
| LEU | 75* | LEU | 999 | | | | | | | |
| LEU | 78 | PHE | 982 | VAL | 17 | | | | | |
| LEU | 82 | LEU | 982 | PHE | 17 | | | | | |
| TYR | 85 | PHE | 887 | VAL | 2 | ILE | 16 | TYR | 94 | |
| LEU | 89 | LEU | 637 | PHE | 314 | TRP | 48 | | | |
| LEU | 103 | VAL | 357 | ALA | 78 | LEU | 269 | ILE | 295 | |
| LEU | 106 | LEU | 945 | VAL | 54 | | | | | |
| VAL | 110 | ILE | 445 | VAL | 405 | LEU | 149 | | | |
| PHE | 113 | LEU | 999 | | | | | | | |
| ALA | 114* | ALA | 999 | | | | | | | |
| ILE | 117* | ILE | 938 | VAL | 61 | | | | | |
| VAL | 151 | ILE | 999 | | | | | | | |
| LEU | 152* | LEU | 999 | | | | | | | |
| VAL | 153 | ILE | 585 | VAL | 414 | | | | | |
| ALA | 154* | ALA | 999 | | | | | | | |
| LEU | 157 | LEU | 797 | VAL | 18 | ILE | 184 | | | |
| PHE | 160 | PHE | 551 | TRP | 448 | | | | | |
| LEU | 161 | LEU | 843 | PHE | 156 | | | | | |
| VAL | 167 | ALA | 999 | | | | | | | |
| LEU | 168 | PHE | 999 | | | | | | | |

*position where Monte Carlo didn't find an alternative and where the top amino acid is the wild type

FIG.—5

Table 5. Core3 - Monte Carlo Analysis (Ground State and Allowed Amino Acids and Their Number of Occurrences (For the Top 1000 Sequences)

| hG-CSF | Position | Ground State | | | | | | | |
|---|---|---|---|---|---|---|---|---|---|
| CYS | 17 | LEU 585 | VAL 35 | ILE 379 | | | | | |
| VAL | 21 | VAL 551 | ALA 15 | ILE 291 | PHE 141 | TYR 1 | | | |
| ILE | 24 | ILE 657 | ALA 31 | VAL 303 | LEU 8 | | | | |
| GLY | 28 | ALA 928 | LEU 71 | | | | | | |
| LEU | 31 | LEU 888 | VAL 111 | | | | | | |
| LYS | 35 | ILE 785 | VAL 214 | | | | | | |
| LEU | 41* | LEU 999 | | | | | | | |
| LEU | 47* | LEU 999 | | | | | | | |
| LEU | 54* | LEU 999 | | | | | | | |
| ILE | 56* | ILE 999 | | | | | | | |
| LEU | 75* | LEU 999 | | | | | | | |
| LEU | 78 | PHE 692 | ALA 10 | VAL 149 | LEU 12 | | | | |
| LEU | 82 | LEU 851 | ALA 12 | PHE 136 | | | | | |
| TYR | 85 | PHE 636 | TRP 363 | | | | | | |
| LEU | 88* | LEU 999 | | | | | | | |
| LEU | 89 | PHE 674 | LEU 214 | TRP 111 | | | | | |
| LEU | 92 | PHE 999 | | | | | | | |
| ILE | 95* | ILE 999 | | | | | | | |
| LEU | 99 | LEU 999 | ILE 111 | | | | | | |
| LEU | 103 | LEU 888 | VAL 106 | LEU 294 | ILE 291 | | | | |
| LEU | 106 | LEU 893 | ALA 14 | PHE 44 | | | | | |
| VAL | 110 | VAL 400 | ALA 1 | | | | | | |
| PHE | 113 | LEU 954 | | | | | | | |
| ALA | 114* | ALA 999 | | | | | | | |
| ILE | 117 | ILE 790 | ALA 15 | VAL 168 | LEU 5 | PHE 20 | ILE 75 | TYR 61 | TRP 1 |

FIG._6A

Table 5. Core3 - Monte Carlo Analysis (Ground State and Allowed Amino Acids and Their Number of Occurrences (For the Top 1000 Sequences)

| hG-CSF | Position | Ground State | | | | | | |
|---|---|---|---|---|---|---|---|---|
| PHE | 140* | PHE | 999 | | | | | |
| VAL | 151 | ILE | 999 | | | | | |
| LEU | 152* | LEU | 999 | | | | | |
| VAL | 153 | ILE | 999 | | | | | |
| ALA | 154* | ALA | 999 | | | | | |
| LEU | 157 | LEU | 694 | ALA | 22 | VAL | 179 | ILE 104 |
| PHE | 160 | PHE | 574 | TRP | 425 | | | |
| LEU | 161 | LEU | 784 | ALA | 6 | VAL | 55 | PHE 154 |
| LEU | 168 | PHE | 999 | | | | | |

*position where Monte Carlo didn't find an alternative and where the top amino acid is the wild type

FIG._6B

Table 6. Bndry4_2 - Monte Carlo Analysis (Ground State and Allowed Amino Acids and Their Number of Occurrences (For the Top 1000 Sequences)

| hG-CSF | Position | Ground State | | | | | | | |
|---|---|---|---|---|---|---|---|---|---|
| LEU | 14 | ILE 998 | | | | | | | |
| GLN | 20 | LEU 999 | | | | | | | |
| ASP | 27 | GLU 999 | | | | | | | |
| GLN | 32 | ILE 999 | | | | | | | |
| LYS | 34 | LYS 717 | ILE 209 | GLU 73 | | | | | |
| THR | 38 | VAL 409 | ILE 188 | GLU 237 | LYS 154 | | | | |
| GLN | 77* | GLN 999 | | | | | | | |
| HIS | 79 | LEU 999 | | | | | | | |
| LEU | 84* | LEU 999 | | | | | | | |
| ALA | 91 | LYS 999 | | | | | | | |
| LEU | 99 | VAL 759 | LEU 193 | | | | | | |
| THR | 102 | LEU 562 | ILE 404 | | | | | | |
| GLN | 107 | ILE 993 | | | | | | | |
| VAL | 109 | GLU 525 | VAL 474 | | | | | | |
| THR | 116 | ILE 749 | LEU 198 | LYS 52 | | | | | |
| GLN | 120 | LEU 999 | | | | | | | |
| GLN | 145 | GLN 650 | GLU 349 | | | | | | |
| ARG | 146 | LYS 891 | GLN 108 | | | | | | |
| ARG | 147 | GLU 999 | | | | | | | |
| ALA | 148 | THR 401 | ALA 268 | ASP 330 | | | | | |
| SER | 155 | ILE 999 | | | | | | | |
| HIS | 156 | LEU 999 | | | | | | | |
| SER | 164 | ALA 999 | | | | | | | |
| HIS | 170 | HSP 380 | LEU 111 | GLU 248 | GLN 227 | | | | |

*position where Monte Carlo didn't find an alternative and where the top amino acid is the wild type

FIG._7

Table 7. Bndry4_core4 - Monte Carlo Analysis (Ground State and Allowed Amino Acids and Their Number of Occurrences (For the Top 1000 Sequences)

| hG-CSF | Position | Ground State | | | | | | | | |
|---|---|---|---|---|---|---|---|---|---|---|
| LEU | 14 | ILE 941 | LEU 58 | ILE 941 | | | | | | |
| GLN | 20 | LEU 999 | | | | | | | | |
| ASP | 27 | GLU 970 | SER 29 | | | | | | | |
| GLN | 32 | LEU 631 | VAL 125 | ILE 243 | | | | | | |
| LYS | 34 | GLU 961 | GLN 22 | LYS 16 | | | | | | |
| THR | 38 | HSP 931 | VAL 19 | ILE 4 | GLU 5 | LYS 40 | | | | |
| GLN | 77* | GLN 999 | | | | | | | | |
| HIS | 79 | LEU 999 | | | | | | | | |
| LEU | 84* | LEU 999 | | | | | | | | |
| ALA | 91 | LYS 999 | | | | | | | | |
| LEU | 99 | LEU 922 | GLU 77 | | | | | | | |
| THR | 102 | LYS 729 | THR 14 | VAL 150 | LEU 2 | ILE 71 | GLU 14 | GLN 19 | | |
| GLN | 107 | ILE 968 | VAL 30 | LEU 1 | | | | | | |
| VAL | 109 | GLU 591 | VAL 402 | ASP 2 | GLN 4 | | | | | |
| THR | 116 | ILE 647 | VAL 15 | LEU 275 | GLU 1 | LYS 61 | | | | |
| GLN | 120 | LEU 999 | | | | | | | | |
| GLN | 145 | GLN 658 | GLU 341 | | | | | | | |
| ARG | 146 | LYS 857 | GLN 142 | | | | | | | |
| ARG | 147 | GLU 998 | LYS 1 | | | | | | | |
| ALA | 148 | ASP 359 | ALA 310 | THR 330 | | | | | | |
| SER | 155 | ILE 999 | | | | | | | | |
| HIS | 156 | LEU 999 | | | | | | | | |
| SER | 164 | ALA 999 | | | | | | | | |
| HIS | 170 | HSP 380 | ASP 26 | LEU 109 | GLU 239 | GLN 214 | LYS 31 | | | |

*position where Monte Carlo didn't find an alternative and where the top amino acid is the wild type

FIG._8

Table 8. Bndry4_AD - Monte Carlo Analysis (Ground State and Allowed Amino Acids and Their Number of Occurrences (For the Top 1000 Sequences)

| Position | Ground State | | | | | | |
|---|---|---|---|---|---|---|---|
| 14 | ILE | 887 | | | | | |
| 20 | LEU | 999 | | | | | |
| 27 | GLU | 984 | | | | | |
| 32 | ILE | 931 | LEU | 112 | | | |
| 34 | GLU | 357 | ILE | 68 | GLN | 223 | LYS 277 |
| 38 | VAL | 287 | ILE | 133 | HSP | 225 | GLU 217 | LYS 123 |
| 145 | GLN | 605 | GLU | 394 | | | |
| 146 | LYS | 786 | GLN | 213 | | | |
| 147 | GLU | 962 | | | | | |
| 148 | THR | 373 | ALA | 305 | ASP | 321 | |
| 155 | ILE | 976 | | | | | |
| 156 | LEU | 994 | | | | | |
| 164 | ALA | 999 | | | | | |
| 170 | HSP | 304 | ASP | 55 | LEU | 136 | GLU 230 | GLN 209 | LYS 62 |

*position where Monte Carlo didn't find an alternative and where the top amino acid is the wild type

FIG._9

Table 9. Bndry4_AD_core4 - Monte Carlo Analysis (Ground State and Allowed Amino Acids and Their Number of Occurrences (For the Top 1000 Sequences)

| Position | Ground State | | | | | | |
|---|---|---|---|---|---|---|---|
| 14  | ILE | 896 | LEU | 103 | | | |
| 20  | LEU | 999 | | | | | |
| 27  | GLU | 996 | | | | | |
| 32  | LEU | 523 | VAL | 194 | ILE | 271 | |
| 34  | GLU | 400 | GLN | 207 | LYS | 341 | |
| 38  | VAL | 300 | ILE | 89  | HSP | 277 | GLU 203 LYS 130 |
| 145 | GLN | 623 | GLU | 376 | | | |
| 146 | LYS | 820 | GLN | 179 | | | |
| 147 | GLU | 986 | | | | | |
| 148 | ASP | 344 | ALA | 332 | THR | 323 | |
| 155 | ILE | 998 | | | | | |
| 156 | LEU | 996 | | | | | |
| 164 | ALA | 999 | | | | | |
| 170 | HSP | 330 | LEU | 134 | GLU | 234 | GLN 216 |

*position where Monte Carlo didn't find an alternative and where the top amino acid is the wild type

FIG._10

Core3
ATGACTCCATTAGTCCAGCTTCCTCTGCCGCAAAGCTTCCTCTGCTGAAACTGCTGGAACAGGTTCGTAAAATCCAGGGTGATGC
AGCTGCTCTGCAGGAGAAAAATCTGCGCTACCTACAAACTGTGCCATCCGGAAGAACTGGTTCTGCTGGGTCACTCCCTGGTATCC
CGTGGGCGCCGCTGAGCTCCTGCCGCAGGCTCTGCAGCTGGCTGGTTGCCTGTCCCAATTCCACAGCGGCCTTTTCCTGTTC
CAGGGTCTGTTCCAGGCTGTCCAGGGCTATCCCCCGAACTGGGCTCCGGCTGCGAAGGTATGCGGTCTGACCGTCGCTGACCTGGC
TACCACCATCTGGCAGCAGCAGAATGGAAGAACTGGATCCTGATCGCTGCAGCGTGGCATCCTGATCGCCTAGCCACCTGACCGTCGCCACCTG
CTTTCCAGCGTCGCCAGGTGCCAGTCCGTTCGACACCACTTCCGAAGAGCTCCTGCAAGTTTCCTACCGTGTTTCCGTCACCTG
GCTCAGCCGTGA

FIG._11A

Core4
ATGACTCCATTAGTCCAGCTTCCTCTGCCGCAAAGCTTCCTCTGCTGAAACTGCTGGAACAGGTTCGTAAAATCCAGGGTGATGC
AGCTGCTCTGCAGGAGAAAAATCTGTGCCATCCGGAAGAACTGTTCTGCTGGGTCACTCCCTGGTATCC
CGTGGGCGCCGCTGAGCTCCTGCCGCAGGCTCTGCAGCTGGCTGGTTGCCTGTCCCAATTCCACAGCGGCCTTTTCCTGTTC
CAGGGTCTGTTCCAGGCTGTCAAGTCTATCCCCGAACTGGGCTCCGGCTATGGCGTTGACATCGCTGACCTGGC
TACCACCATCTGGCAGCAGCAGCAGAATGGAAGAACTGGATCCTGATCGCTGCAGCGTGGCATCCTGATCGCCTAGCCACCTGACCGTCGCCACCTG
CTTTCCAGCGTCGCCAGGTGCCAGTCCGTTCGACACCACTTCCGAAGAGCTCCTGCAAGTTTCCTACCGTGTTTCCGTCACCTG
GCTCAGCCGTGA

FIG._11B

Core4v
ATGACTCCATTAGTCCAGCTTCCTCTGCCGCAAAGCTTCCTCTGCTGAAACTGCTGGAACAGATCCGTAAAATCCAGGGTGATGC
AGCTGCTCTGCAGGAGAAAAATCTGTGCCATCCGGAAGAACTGTTCTGCTGGGTCACTCCCTGGTATCC
CGTGGGCGCCGCTGAGCTCCTGCCGCAGGCTCTGCAGCTGGCTGGTTGCCTGTCCCAATTCCACAGCGGCCTTTTCCTGTTC
CAGGGTCTGTTCCAGGCTGTCAAGTCTATCCCCGAACTGGGCTCCGGCTATGGCGTTGACATCGCTGACCTGGC
TACCACCATCTGGCAGCAGCAGCAGAATGGAAGAACTGGATCCTGATCGCTGCAGCGTGGCATCCTGATCGCCTAGCCACCTGACCGTCGCCACCTG
CTTTCCAGCGTCGCCAGGTGCCAGTCCGTTCGACACCACTTCCGAAGAGCTCCTGCAAGTTTCCTACCGTGTTTCCGTCACCTG
GCTCAGCCGTGA

FIG._11C

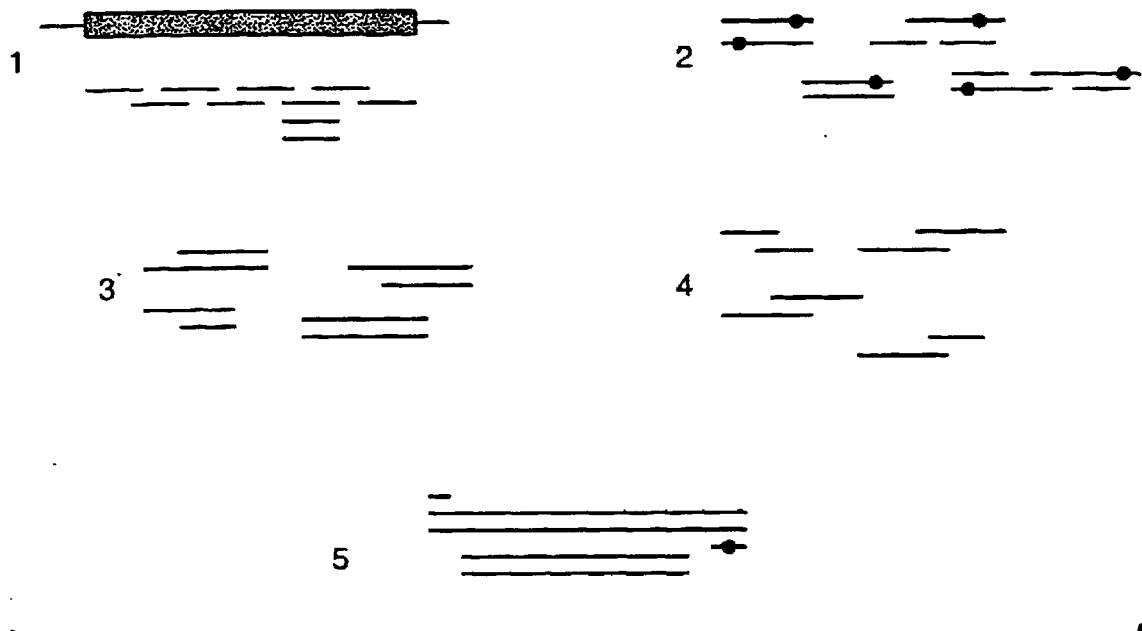
FIG._12
| | -Melting Temperature ($T_m$) | |
|---|---|---|
| | $T_m$ (°C) | Extinction Coefficient ($M^{-1}$ $cm^{-1}$) |
| hG-CSFwt | 60 | 15720 |
| core4 | 72 | 14230 |
| core4v | 61 | 19730 |
| core3 | 58 | 14230 |
| sm0* | 63 | 15720 |
| fm4* | 63 | 15720 |
| fm7* | 70 | 14230 |
* Derived by reverting some core4 or core3 mutant positions to wild type
FIG._16

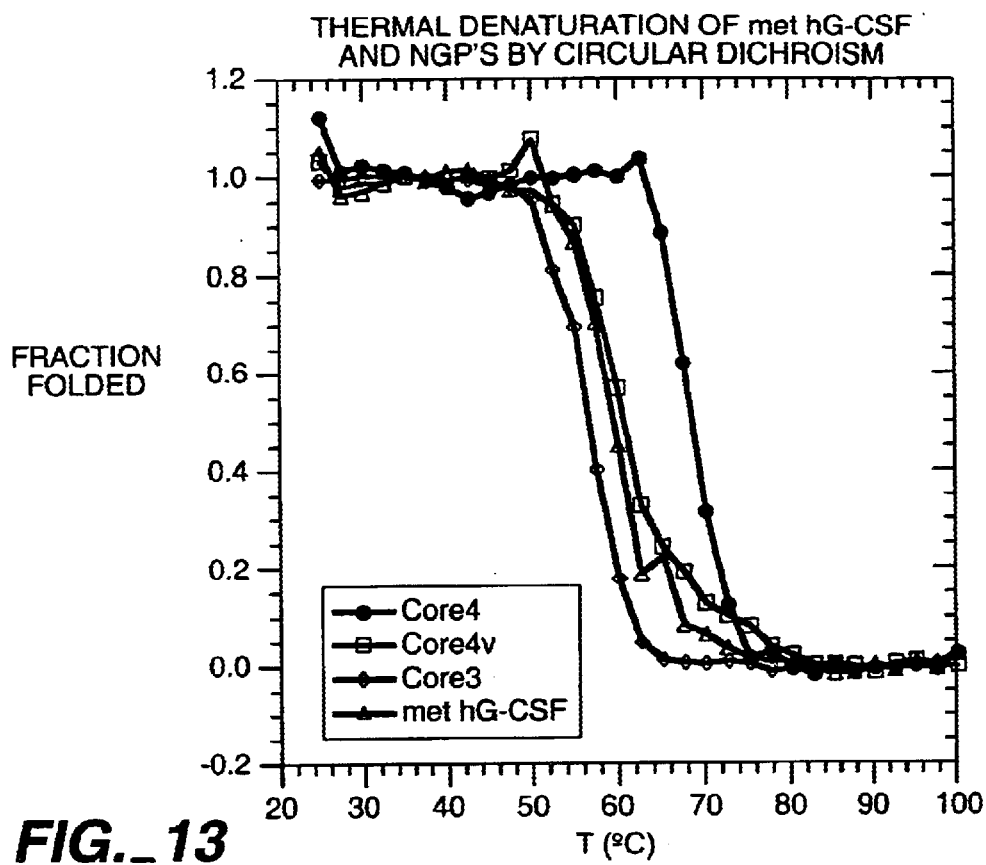
FIG._13
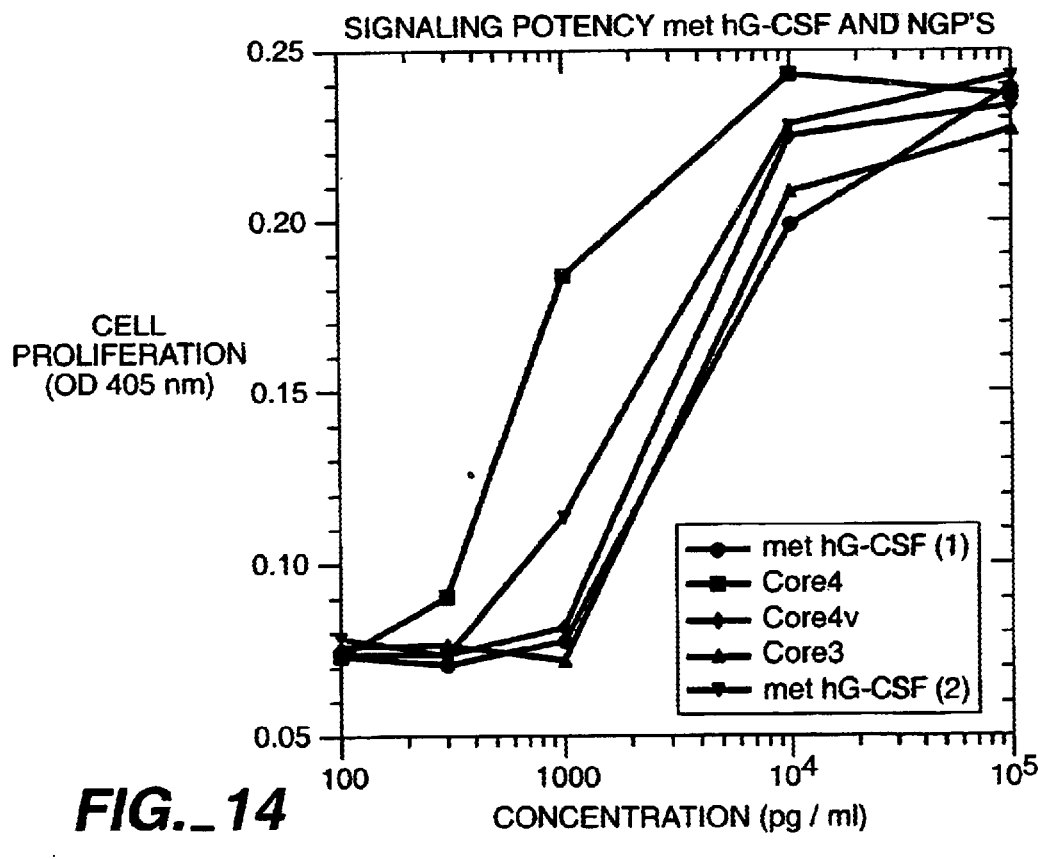
FIG._14

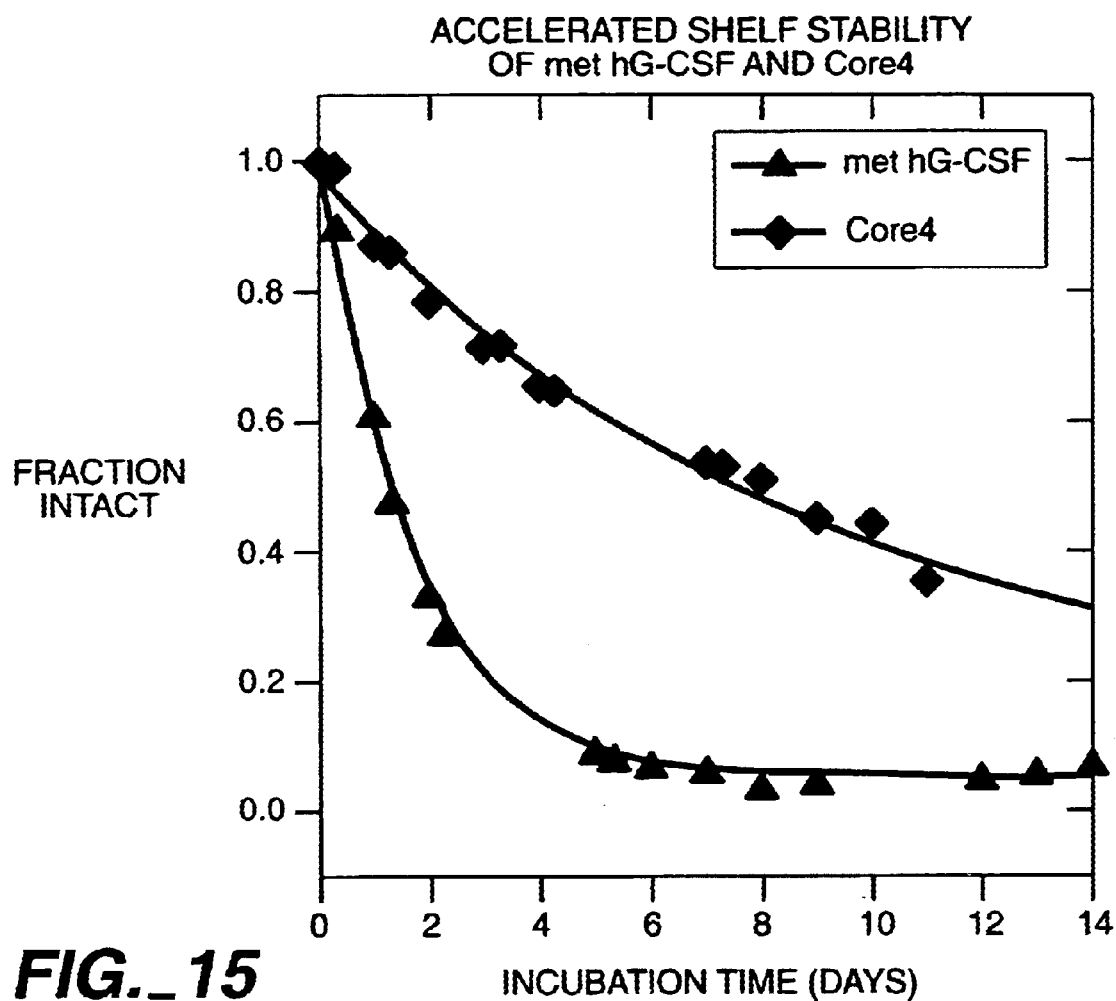
FIG._15

NUCLEIC ACIDS AND PROTEIN VARIANTS OF HG-CSF WITH GRANULOPOIETIC ACTIVITY

This application is a continuing application of U.S. Ser. Nos. 60/115,131, filed Jan. 6, 1999 and of 60/118,831, filed Feb. 5, 1999.

FIELD OF THE INVENTION

The invention relates to novel granulopoietic activity (GPA) proteins and nucleic acids. The invention further relates to the use of the GPA proteins in the treatment of G-CSF related disorders.

BACKGROUND OF THE INVENTION

The colony stimulating factors are a class of protein hormones that stimulate the proliferation and the function of specific blood cell types such as granulocytes. Granulocytes engulf and devour microbial invaders and cell debris and thus are crucial to infection response. Granulocytes have only a 6–12 hour life span in the bloodstream and are destroyed as they function. Accordingly, it necessary for the blood marrow stem cells to rapidly and constantly generate granulocytes. Granulocyte colony stimulating factor (G-CSF) is a protein that is essential for the proliferation and differentiation of granulocytes, particularly neutrophils.

However, as a result of their fast turnover, the granulocyte count falls rapidly and markedly upon bone marrow damage, for example from treatment with traditional cancer treatments, including chemotherapeutic agents and radiation, or immunologic disorders including AIDS. Accordingly, treatment with hG-CSF has been shown to be efficacious in minimizing some of the side effects of cancer therapies, as well as in treatment of suppressed immune systems.

However, wild-type hG-CSF has several disadvantages, including storage stability problems as well as a short half-life in the blood stream.

To this end, variants of G-CSF are known; see for example U.S. Pat. Nos. 5,214,132; 5,399,345; 5,790,421; 5,581,476; 4,999,291; 4,810,643; 4,833,127; 5,218,092; 5,362,853; 5,830,705; 5,580,755; 5,399,345 and 5,416,195 and references cited therein.

However, a need still exists for proteins exhibiting both significant stability and granulopoietic activity. Accordingly, it is an object of the invention to provide granulopoietic activity (GPA) proteins, nucleic acids and antibodies for the treatment of neutrophil disorders.

SUMMARY OF THE INVENTION

In accordance with the objects outlined above, the present invention provides non-naturally occurring GPA proteins (e.g. the proteins are not found in nature) comprising amino acid sequences that are less than about 95–97% identical to hG-CSF. The GPA proteins have at least one biological property of a G-CSF protein; for example, the GPA proteins will stimulate cells with a G-CSF receptor to proliferate. Thus the invention provides GPA proteins with amino acid sequences that have at least about 5 amino acid substitutions as compared to the hG-CSF sequence shown in FIG. 1.

In a further aspect, the present invention provides non-naturally occurring GPA conformers that have three dimensional backbone structures that substantially correspond to the three dimensional backbone structure of hG-CSF. The amino acid sequence of the conformer and the amino acid sequence of the hG-CSF are less than about 95% identical. In one aspect, at least about 90% of the non-identical amino acids are in a core region of the conformer. In other aspects, the conformer have at least about 100% of the non-identical amino acids are in a core region of the conformer.

In an additional aspect, the changes are selected from the amino acid residues at positions selected from 14, 17, 20, 21, 24, 27, 28, 31, 32, 34, 38, 78, 79, 85, 89, 91, 99, 102, 103, 107, 109, 110, 113, 116, 120, 145, 146, 147, 148, 151, 153, 155, 156, 157, 160, 161, 164, 168 and 170. Preferred embodiments include at least about 5 or 10 variations.

In a further aspect, the invention provides recombinant nucleic acids encoding the non-naturally occurring GPA proteins, expression vectors comprising the recombinant nucleic acids, and host cells comprising the recombinant nucleic acids and expression vectors.

In an additional aspect, the invention provides methods of producing the GPA proteins of the invention comprising culturing host cells comprising the recombinant nucleic acids under conditions suitable for expression of the nucleic acids. The proteins may optionally be recovered.

In a further aspect, the invention provides pharmaceutical compositions comprising a GPA protein of the invention and a pharmaceutical carrier.

In an additional aspect, the invention provides methods for treating a G-CSF responsive condition comprising administering a GPA protein of the invention to a patient. The C-CSF condition may be myelo-suppresive therapy, chronic neutropenia, or peripheral blood progenitor cell collection.

BRIEF DESCRIPTION OF THE DRAWINGS

FIG. 1 depicts the nucleic acid (SEQ ID NO:1) and amino acid (SEQ ID NO:2) sequences of human G-CSF.

FIG. 2 depicts the variable residues in each GPA set.

FIG. 3 (SEQ ID NOS:2–15) depicts some preferred GPA sequences. The top line (SEQ ID NO:15) is the hG-CSF sequence . Any residue for which a change is not noted remains the same as the hG-CSF sequence. The second line (SEQ ID NO:3) is a GPA protein, bndry4_2, with variable boundary residues; 24 different positions were allowed to vary. The third line (SEQ ID NO:4) is a GPA protein, bndry4_core4, with boundary variable residues; this utilized 24 different boundary positions but used the optimal sequence from the core4 design as the starting template. The fourth line (SEQ ID NO:5) is a GPA protein, bndry4_AD, with boundary variable residues; however, the boundary residues were chosen on the outer two helices (A and D; 14 variable residue positions) since initial calculations suggested that the most pronounced changes in helical propensity result from modifications at these locations; improvements in helical propensity might lead to improved stability. The fifth line (SEQ ID NO:6) is a GPA protein, bndry4_AD_core4 with 14 variable boundary residues; again suing the optimal sequence from the core4 design as the starting template. The sixth line (SEQ ID NO:7) is a GPA protein, core4, that utilized 26 different variable core positions. The seventh line (SEQ ID NO:8) is a GPA protein, core4_V167A, that utilized 25 variable core positions. The eighth line (SEQ ID NO:9) is a GPA protein, core3, that had 34 core variable positions.

FIG. 4 depicts the Monte Carlo analysis of the core4 GPA sequence. At the left is shown the hG-CSF sequence position numbers are shown in the second column, the ground state sequence is shown in the third column and the number of occurrences of all amino acids found in the top 1000 Monte Carlo sequences is shown in the last columns. At position 17, for example, the hG-CSF a mino acid is cysteine; in GPA proteins, 73.6% of the top 1000 sequences had leucine at this position, and 22.9% of the sequences had isoleucine.

FIG. 5 depicts the Monte Carlo analysis of the core4v GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns. At position 17, for example, the hG-CSF amino acid is cysteine; in GPA proteins, 69.7% of the top 1000 sequences had leucine at this position, and 5.1% of the sequences had valine; and 25.1% of the sequences had isoleucine.

FIG. 6 depicts the Monte Carlo analysis of the core3 GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns.

FIG. 7 depicts the Monte Carlo analysis of the bndry4_2 GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns.

FIG. 8 depicts the Monte Carlo analysis of the bndry4_core4 GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns.

FIG. 9 depicts the Monte Carlo analysis of the bndry4_AD GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns.

FIG. 10 depicts the Monte Carlo analysis of the bndry4_AD_core4 GPA sequence. At the left is shown the hG-CSF sequence; position numbers are shown in the second column, the ground state sequence is shown in the third column and the number of occurrences of all amino acids found in the top 1000 Monte Carlo sequences is shown in the last columns.

FIGS. 11A, 11B and 11C depict the gene sequences for three GPA proteins: FIG. 11A (SEQ ID NO:16) is the core3 GPA protein, FIG. 11B (SEQ ID NO:17) is the core4 GPA protein, and FIG. 11C (SEQ ID NO:18) is the core4v GPA protein.

FIG. 12 depicts the synthesis of a full-length gene and all possible mutations by PCR. Overlapping oligonucleotides corresponding to the full-length gene (black bar, Step 1) are synthesized, heated and annealed. Addition of Pfu DNA polymerase to the annealed oligonucleotides results in the 5' to 3' synthesis of DNA (Step 2) to produce longer DNA fragments (Step 3). Repeated cycles of heating, annealing (Step 4) results in the production of longer DNA, including some full-length molecules. These can be selected by a second round of PCR using primers (arrowed) corresponding to the end of the full-length gene (Step 5).

FIG. 13 depicts the thermal stability of met hG-CSF and several GPA proteins by circular dichroism (CD) spectroscopy. CD directly measures secondary structure content of a protein and can track the loss of structure in response to temperature or chemical denaturants. FIG. 13 shows the increased thermal stability of core4 relative to met hG-CSF.

FIG. 14 depicts the cell proliferation response to met hG-CSF and 3 novel GPA proteins. Cell proliferation of BaF/3 cells expressing hG-CSF receptor is shown as monitored by BrdU incorporation, plotted against protein concentration. BrdU incorporation is assessed by fluorescent ELISA. The figure shows the increased biological activity of core4 relative to met hG-CSF.

FIG. 15 depicts the kinetics of storage stability of met hG-CSF and core4 monitored by size exclusion chromatography HPLC. The two proteins were incubated in 5% sorbitol, 10 mM sodium acetate, 0.004% Tween-80 at pH 4.0 and and stored at 50° C. The protein concentration was 300 ug/ml. Monomeric protein was considered intact.

FIG. 16 depicts the melting temperature (Tm) and extinction coefficients of hG-CSF and some of the novel GPA proteins of the invention.

DETAILED DESCRIPTION OF THE INVENTION

The present invention is directed to novel proteins and nucleic acids possessing granulopoietic activity (sometimes referred to herein as "GPA proteins" and "GPA nucleic acids"). The proteins are generated using a system previously described in WO98/47089 and U.S. Ser. No. 09/127,926, both of which are expressly incorporated by reference in their entirety, that is a computational modeling system that allows the generation of extremely stable proteins without necessarily disturbing the biological functions of the protein itself. In this way, novel GPA proteins and nucleic acids are generated, that can have a plurality of mutations in comparison to the wild-type enzyme yet retain significant activity.

The computational method used to generate and evaluate the GPA proteins of the invention is briefly described as follows. In a preferred embodiment, the computational method used to generate the primary library is Protein Design Automaton (PDA), as is described in U.S. Ser. Nos. 60/061,097, 60/043,464, 60/054,678, 09/127,926 and PCT US98/07254, all of which are expressly incorporated herein by reference. Briefly, PDA can be described as follows. A known protein structure is used as the starting point. The residues to be optimized are then identified, which may be the entire sequence or subset(s) thereof. The side chains of any positions to be varied are then removed. The resulting structure consisting of the protein backbone and the remaining sidechains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include, but are not limited to, the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. In addition, as will be appreciated by those in the art, a Monte Carlo search may be done from a DEE run that is not completed; that is, a partial DEE run that has a number of sequences may be used to generate a Monte Carlo list.

As outlined in U.S. Ser. No. 09/127,926, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimizabon of the structure is run, to relax the hydrogens as well as the other atoms, bond angles and bond lengths. In a preferred embodiment, this is done by doing a number of steps of conjugate gradient minimizabon (Mayo et al., *J. Phys. Chem.* 94:8897 (1990)) of atomic coordinate positions to minimize the Dreiding force field with no electrostatics. Generally from about 10 to about 250 steps is preferred, with about 50 being most preferred.

The GPA backbone structure contains at least one variable residue position. Each GPA residue that can differ from the hG-CSF protein at an equivalent position is called a "variable residue". As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occurring) protein may have one of at least 20 amino acids, in any number of rotamers. By "variable residue position" herein is meant an amino acid position of the protein to be designed that is not fixed in the design method as a specific residue or rotamer, generally the wild-type hG-CSF residue or rotamer.

In a preferred embodiment, all of the residue positions of the protein are variable. That is, every amino acid side chain may be altered in the methods of the present invention.

In an alternate preferred embodiment, only some of the residue positions of the protein are variable, and the remainder are "fixed", that is, they are identified in the three dimensional structure as being a particular amino acid in a set conformation. In some embodiments, a fixed position is left in its original conformation (which may or may not correlate to a specific rotamer of the rotamer library being used). Alternatively, residues may be fixed as a non-wild type residue; for example, when known site-directed mutagenesis techniques have shown that a particular residue is desirable (for example, to eliminate a proteolytic site or alter the active site), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues. For example, residues which are known to be important for biological activity, such as the residues which form the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in a conformation or as a single rotamer, or "floated".

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable biological activity but with a preservation of binding, etc.

In a preferred embodiment, each variable position is classified as either a core, surface or boundary residue position, although in some cases, as explained below, the variable position may be set to glycine to minimize backbone strain.

In one embodiment, only core residues are variable residues; alternate embodiments utilize methods for designing GPA proteins containing core, boundary and surface variable residues; core and surface variable residues; core and boundary variable residues; surface and boundary variable residues; as well as surface variable residues alone, or boundary variable residues alone. In general, preferred embodiments do not utilize surface variable residues, as this can lead to undesirable antigenicity; however, in applications that are not related to therapeutic use of the GPA proteins, it may be desirable to alter surface residues.

The classification of residue positions as core, surface or boundary may be done in several ways, as will be appreciated by those in the art and outlined in WO98/47089, hereby incorporated by reference in its entirety. In a preferred embodiment, the classification is done via a visual scan of the original protein backbone structure, including the side chains, and assigning a classification based on a subjective evaluation of one skilled in the art of protein modelling. Alternatively, a preferred embodiment utilizes an assessment of the orientation of the Cα-Cβ vectors relative to a solvent accessible surface computed using only the template Cα atoms. In a preferred embodiment, the solvent accessible surface for only the Cα atoms of the target fold is generated using the Connolly algorithm with a probe radius ranging from about 4 to about 12 Å, with from about 6 to about 10 Å being preferred, and 8 Å being particularly preferred. The Cα radius used ranges from about 1.6 Å to about 2.3 Å, with from about 1.8 to about 2.1 Å being preferred, and 1.95 Å being especially preferred. A residue is classified as a core position if a) the distance for its Cα, along its Cα-Cβ vector, to the solvent accessible surface is greater than about 4–6 Å, with greater than about 5.0 Å being especially preferred, and b) the distance for its Cβ to the nearest surface point is greater than about 1.5–3 Å, with greater than about 2.0 Å being especially preferred. The remaining residues are classified as surface positions if the sum of the distances from their Cα, along their Cα-Cβ vector, to the solvent accessible surface, plus the distance from their Cβ to the closest surface point was less than about 2.54 Å, with less than about 2.7 Å being especially preferred. All remaining residues are classified as boundary positions.

Suitable core and boundary positions for GPA proteins are outlined below.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the α scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle (that is, the dihedral angle defined by 1) the carbonyl carbon of the preceding amino acid; 2) the nitrogen atom of the current residue; 3) the α-carbon of the current residue; and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total}=nE_{vdw}+nE_{as}+nE_{h\text{-}bonding}+nE_{ss}+nE_{elec} \qquad \text{Equation 1}$$

In Equation 1, the total energy is the sum of the energy of the van der Waals potential ($E_{vdw}$), the energy of atomic solvation ($E_{as}$), the energy of hydrogen bonding ($E_{h\text{-}bonding}$), the energy of secondary structure ($E_{ss}$ and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926 and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdW}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdW}$ is calculated for each possible rotamer pair at every two variable residue positions. For the atomic solvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

Once the singles and doubles energies are calculated and stored, the next step of the computational processing may occur. As outlined in U.S. Ser. No. 09/127,926 and PCT US98/07254, preferred embodiments utilize a Dead End Elimination (DEE) step, and preferably a Monte Carlo step.

The computational processing results in a set of optimized GPA protein sequences. These optimized GPA protein sequences are generally significantly different from the wild-type hG-CSF sequence from which the backbone was taken.

Thus, in the broadest sense, the present invention is directed to GPA proteins that have granulopoietic activity. By "granulopoietic activity" or "GPA" herein is meant that the protein exhibits at least one, and preferably more, of the biological functions of a granulocyte-colony stimulating factor (G-CSF), as defined below.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, generally depending on the method of synthesis. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22, 1998 and Tang et al., Abstr. Pap Am. Chem. S218:U138-U138 Part 2 Aug. 22, 1999, both of which are expressly incorporated by reference herein.

The GPA proteins of the invention exhibit at least one biological function of a G-CSF. By "granulocyte colony stimulating factor" or "G-CSF" herein is meant a wild type G-CSF. The G-CSF may be from any number of organisms, with G-CSFs from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (this is sometimes referred to herein as hG-CSF, the sequence of which is depicted in FIG. 1). As will be appreciated by those in the art, GPAs based on G-CSFs from mammals other than humans may find use in animal models of human disease. The GI numbers for a variety of mammalian species is as follows: bovine 442671; dog 442673; sheep 310382; cat CAA69853; pig 2411469; mouse 309248; rat 1680659.

The GPA proteins of the invention exhibit at least one biological function of a G-CSF. By "biological function" or "biological property" herein is meant any one of the properties or functions of a G-CSF, including, but not limited to, the ability to stimulate cell proliferation, particularly of hematopoetic stem cells to produce granulocytes and particularly neutrophils; the ability to treat severe chronic neutropenia; the use in harvesting peripheral blood progenitor cells; the ability to enhance bone marrow transplantation therapy; as well as the stimulation of CFU -Gm type cells.

In a preferred embodiment, the biological function is granulopoietic activity (GPA). GPA is defined as the ability of the compound to stimulate cells that have a G-CSF receptor to proliferate. However, in some embodiments, GPA proteins may not possess GPA activity.

In a preferred embodiment, the assay system used to determine GPA is an in-vitro system as described in the examples, using Ba/F3 cells stably transfected with the gene encoding the human Class 1 G-CSF receptor; see Young et al. Protein Sci. 6:1228–1236 (1997), hereby expressly incorporated by reference in its entirety. In this system, cell proliferation is measured as a function of BrdU incorporation, which is incorporated into the nucleic acid of the proliferating cells. An increase above background of at least about 20%, with at least about 50% being preferred and at least about 100%, 500% and 1000% being especially preferred is an indication of GPA. An alternative assay is the CFU-GM cell assay as described in Zsebo et al, Immunobiology 172:175–184 (1986), also expressly incorporated by reference in its entirety.

In a preferred embodiment, an in-vivo system can be used to assay for GPA. For example, a suitable system is as described in U.S. Pat. No. 4,999,291, hereby incorporated by reference in its entirety. In general, in vivo assays require the administration of the GPA protein (or, in the case of gene therapy, of the GPA nucleic acid) to a suitable animal, followed by monitoring of the granulocyte count (or in some cases monitoring lymphocytes can be done) of the animal. In general, increases in neutrophil, granulocyte or lymphocyte counts without corresponding erythrocyte counts is indicative of G-CSF. Similarly, a useful in vivo assay system is as follows: male c57BL/6N mice are rendered neutropenic with a single intraperitoneal injection of 200 mg/kg cyclophosphamide (CPA). Beginning 24 hrs later and for 4 consecutive days from the day after the dosing with CPA, the mice are given a daily intravenous injection of 100 ug/kg of rhG-CSF, novel granulopoietic protein, or control vehicle. Granulopoietic activity is assayed on day 5 by bleeding the mice retro-orbitally and counting the number of white blood cells and polymorphonuclear neutrophils. See Hattori et al., Blood 75:1228–1233 (1990), expressly incorporated by reference in its entirety.

In a preferred embodiment, the antigenic profile in the host animal of the GPA protein is similar, and preferably identical, to the antigenic profile of the host G-CSF; that is, the GPA protein does not significantly stimulate the host organism (e.g. the patient) to an immune response; that is, any immune response is not clinically relevant and there is no allergic response or neutralization of the protein by an antibody. That is, in a preferred embodiment, the GPA protein does not contain additional or different epitopes from the G-CSF. By "epitope" or "determinant" herein is meant a portion of a protein which will generate and/or bind an antibody. Thus, in most instances, no significant amount of antibodies are generated to a GPA protein. In general, this is accomplished by not significantly altering surface residues, as outlined below nor by adding any amino acid residues on the surface which can become glycosylated, as novel glycosylation can result in an immune response.

The GPA proteins and nucleic acids of the invention are distinguishable from naturally occurring G-CSFs. A "naturally occurring G-CSF" is one that exists in nature and includes allelic variations; a representative sequence is the human sequence (hG-CSF) shown in FIG. 1. It should be noted that unless otherwise stated, all positional numbering is based on this human G-CSF sequence. That is, as will be appreciated by those in the art, an alignment of G-CSF proteins and GPA proteins can be done using standard programs, as is outlined below, with the identification of "equivalent" positions between the two proteins. Thus, the GPA proteins and nucleic acids of the invention are non-naturally occurring; that is, they do not exist in nature.

Thus, in a preferred embodiment, the GPA protein has an amino acid sequence that differs from a wild-type G-CSF sequence by at least 3% of the residues. That is, the GPA proteins of the invention are less than about 97% identical to a G-CSF amino acid sequence. Accordingly, a protein is a "GPA protein" if the overall homology of the protein sequence to the amino acid sequence shown in FIG. 1 is preferably less than about 97%, more preferably less than about 95%, even more preferably less than about 90% and most preferably less than 85%. In some embodiments the homology will be as low as about 75 to 80%. Stated differently, based on the hG-CSF sequence of 174 residues, GPA proteins have at least about 5 residues that differ from the hG-CSF sequence (3%), with GPA proteins having from 5 residues to upwards of 30 residues being different from the hG-CSF sequence. In some instances, GPA proteins have 3 or 4 different residues from the hG-CSF sequence. Preferred GPA proteins have 10–24 different residues with from about 10 to about 14 being particularly preferred (that is, 6–8% of the protein is not identical to hG-CSF).

Homology in this context means sequence similarity or identity, with identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, *Adv. Appl. Math.*, 2:482 (1981), by the sequence identity alignment algorithm of Needleman & Wunsch, *J. Mol. Biol.*, 48:443 (1970), by the search for similarity method of Pearson & Lipman, *Proc. Natl. Acad. Sci. U.S.A.*, 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.*, 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., *J. Mol. Biol.*, 215, 403–410, (1990) and Karlin et al., *Proc. Natl. Acad. Sci. U.S.A.*, 90:5873–5787 (1993). A particularly useful BLAST program is the WU-BLAST-2 program which was obtained from Altschul et al., *Methods in Enzymology*, 266:460–480 (1996); http://blast.wustl/edu/blast/README.html]. WU-BLAST-2 uses several search parameters, most of which are set to the default values. The adjustable parameters are set with the following values: overlap span=1, overlap fraction =0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucl. Acids Res.*, 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1, it is understood that in one embodiment, the percentage of sequence identity will be determined based on the number of identical amino acids in relation to the total number of amino acids. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, GPA proteins of the present invention may be shorter or longer than the amino acid sequence shown in FIG. 1. Thus, in a preferred embodiment, included within the definition of GPA proteins are portions or fragments of the sequences depicted herein. Fragments of GPA proteins are considered GPA proteins if a) they share at least one antigenic epitope; b) have at least the indicated homology; c) and preferably have GPA biological activity as defined herein.

In a preferred embodiment, as is more fully outlined below, the GPA proteins include further amino acid variations, as compared to a wild-type G-CSF, than those outlined herein. In addition, as outlined herein, any of the variations depicted herein may be combined in any way to form additional novel GPA proteins.

In addition, GPA proteins can be made that are longer than those depicted in the figures, for example, by the addition of epitope or purification tags, as outlined herein, the addition of other fusion sequences, etc. For example, the GPA proteins of the invention may be fused to other therapeutic proteins such as IL-11 or to other proteins such as Fc or serum albumin for pharmacokinetic purposes. See for example U.S. Pat. Nos. 5,766,883 and 5,876,969, both of which are expressly incorporated by reference.

In a preferred embodiment, the GPA proteins comprise variable residues in core and boundary residues.

hG-CSF core residues are as follows: positions 17, 21, 24, 28, 31, 35, 41, 47, 54, 56, 75, 78, 82, 85, 88, 89, 92, 95, 99, 103, 106, 110, 113, 114, 117, 140, 149, 150, 151, 152, 153, 154, 157, 160, 161 and 168. Accordingly, in a preferred embodiment, GPA proteins have variable positions selected from these positions.

In a preferred embodiment, GPA proteins have variable positions selected solely from core residues of hG-CSF. Alternatively, at least a majority (51%) of the variable positions are selected from core residues, with at least about 75% of the variable positions being preferably selected from core residue positions, and at least about 90% of the variable positions being particularly preferred. A specifically preferred embodiment has only core variable positions altered as compared to hG-CSF.

Particularly preferred embodiments where GPA proteins have variable core positions as compared to hG-CSF are shown in the Figures.

In one embodiment, the variable core positions are altered to any of the other 19 amino acids. In a preferred embodiment, the variable core residues are chosen from Ala, Val, Phe, Ile, Leu, Tyr and Trp. hG-CSF boundary residues are as follows: positions 14, 20, 27, 32, 34, 38, 77, 79, 84, 91, 99, 102, 107, 109, 116, 120, 145, 146, 147, 155, 156, 164 and 170. Accordingly, in a preferred embodiment, GPA proteins have variable positions selected from these positions.

In a preferred embodiment, the boundary core positions are altered to any of the other 19 amino acids. In a preferred embodiment, the variable boundary residues are chose from Ala, Val, Leu, Ile, Asp, Asn, Glu, Gln, Lys, Ser, Thr and His (preferably protonated His).

In a preferred embodiment, the GPA protein of the invention has a sequence that differs from a wild-type G-CSF protein in at least one amino acid position selected from position 14, 17, 20, 21, 24, 27, 28, 31, 32, 34, 38, 78, 79, 85, 89, 91, 99, 102, 103, 107, 109, 110, 113, 116, 120, 145, 146, 147, 148, 151, 153, 155, 156, 157, 160, 161, 164, 168 and 170; see also FIG. 2 which outlines sets of amino acid positions.

Preferred amino acids for each position, including the hG-CSF residue, are shown in FIGS. 3–10. Thus, for example, at position 17, preferred amino acids are Leu, Val and Ile; at position 21, Val, Ile, Phe, Ala, and Tyr; etc.

Preferred changes are as follows: Leu14Ile; Cys17Ala; Cys17Leu; Cys17Ile; Gln20Leu; Val2Ile; Val21Ala; Val21Phe; Val21Tyr; Ile24Ala; Ile24Val; Ile24Leu; Asp27Glu; Asp27Ser; Gly28Ala; Gly28Leu; Leu31Val; Gln32Leu; Gln32Val; Gln32Ile; Lys34Glu; Lys34Gln; Lys35Ile; Lys35Val; Thr38His; Thr38Val; Thr38Ile; Thr38Glu; Thr38Lys; Leu78Phe; Leu78Ala; Leu78Val; Leu78Ile; Leu78Tyr; His79Leu; Leu82Ala; Leu82Phe; Tyr85Val; Tyr85Ile; Tyr85Phe; Tyr85Trp; Leu89Phe; Leu89Trp; Ala91Lys; Leu92Phe; Leu99Glu; Thr102Lys; Thr102Val; Thr102Leu; Thr102Ile Thr102Glu; Thr102Gln; Leu103Val; Leu103Ile; Leu103Ala; Leu106Val; Gln107Ile; Gln107Val; Gln107Leu; Val109Glu; Val109Asp; Val109Gln; Val110Ala; Val110Leu; Val110Ile; Phe113Ala; Phe113Leu; Thr116Ile; Thr116Val; Thr116Leu; Thr116Glu; Thr116Ala; Ile117Val; Ile117Leu; Ile117Phe; Ile117Trp; Gln120Leu; Gln145Glu; Arg146Lys; Arg146Gln; Arg147Glu; Arg147Lys; Ala148Asp; Ala148Thr; Val151Ile; Val153Ile; Ser155Ile; His156Leu; Leu157Ala; Leu157Val; Leu157Ile; Phe160Trp; Leu161Phe; Ser164Ala; Leu157Ile; Phe160Trp; Leu161Phe; Leu161Ala; Leu161Val; Val167Ala; Leu168Phe; His170Asp; His170Leu; His170Glu; His170Gln; and His170Lys. These may be done either individually or in combination, with any combination being possible. However, as outlined herein, preferred embodiments utilize at least four, and preferably more, variable positions in each GPA protein.

Particularly preferred sequences are selected from the group consisting of: C17L, G28A, L78F, Y85F, L103V, V110I, F113L, V151I, V153I and L168F, SEQ ID NO: 7; and L14I, Q20L, D27E, Q32L, K34E, T38H, H79L, A91K, T102K, Q107I, D109E, T116I, Q120L, R146K, R147E, A148D, S155I, H156L, S163A, SEQ ID NO: 18.

In a preferred embodiment, the GPA proteins do not have sole single variable positions at positions 17, 24, 35, 41, 18, 68, 26, 174, 170, 167, 44, 47, 23, 20, 28, 127, 138, 13, 121 or 124. Similarly, preferred embodiments of GPA proteins do not only have two variable positions at 127 and 138 or 37 and 43. In a preferred embodiment, the GPA proteins do not have only three variable positions at 17, 24 and 41; 17, 24 and 35; and 17, 35 and 41. Furthermore, preferred GPA proteins doe not have only four variable positions at 17, 24, 35 and 41.

In a preferred embodiment, the GPA proteins of the invention are hG-CSF conformers. By "conformer" herein is meant a protein that has a protein backbone 3D structure that is virtually the same but has significant differences in the amino acid side chains. That is, the GPA proteins of the invention define a conformer set, wherein all of the proteins of the set share a backbone structure and yet have sequences that differ by at least 3–5%. "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the hG-CSF structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer.

GPA proteins may also be identified as being encoded by GPA nucleic acids. In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence, with lower homology being preferred.

In a preferred embodiment, an GPA nucleic acid encodes an GPA protein. As will be appreciated by those in the art, due to the degeneracy of the genetic code, an extremely large number of nucleic acids may be made, all of which encode the GPA proteins of the present invention. Thus, having identified a particular amino acid sequence, those skilled in the art could make any number of different nucleic acids, by simply modifying the sequence of one or more codons in a way which does not change the amino acid sequence of the GPA.

In one embodiment, the nucleic acid homology is determined through hybridization studies. Thus, for example, nucleic acids which hybridize under high stringency to the nucleic acid sequences shown in FIG. 1 or its complement and encode a GPA protein is considered an GPA gene.

High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The GPA proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequence depicted in FIG. 1 also includes the complement of the sequence. By the term "recombinant nucleic acid"herein is meant nucleic acid, originally formed in vitro, in general, by the manipulation of nucleic acid by endonucleases, in a form not normally found in nature. Thus an isolated GPA nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an GPA protein from one organism in a different organism or host cell. Alternatively, the protein may be made at a significantly higher concentration than is normally seen, through the use of a inducible promoter or high expression promoter, such that the protein is made at increased concentration levels. Furthermore, all of the GPA proteins outlined herein are in a form not normally found in nature, as they contain amino acid substitutions, insertions and deletions, with substitutions being preferred, as discussed below.

Also included within the definition of GPA proteins of the present invention are amino acid sequence variants of the GPA sequences outlined herein and shown in the Figures. That is, the GPA proteins may contain additional variable positions as compared to hG-CSF. These variants fall into one or more of three classes: substitutional, insertional or deletional variants. These variants ordinarily are prepared by site specific mutagenesis of nucleotides in the DNA encoding a GPA protein, using cassette or PCR mutagenesis or other techniques well known in the art, to produce DNA encoding the variant, and thereafter expressing the DNA in recombinant cell culture as outlined above. However, variant GPA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the GPA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed GPA variants screened for the optimal combination of desired activity. Techniques for making substitution mutations at predetermined sites in DNA having a known sequence are well known, for example, M13 primer mutagenesis and PCR mutagenesis. Screening of the mutants is done using assays of GPA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the GPA protein are desired, substitutions are generally made in accordance with the following chart:

Chart 1

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original GPA protein, although variants also are selected to modify the characteristics of the GPA proteins as needed. Alternatively, the variant may be designed such that the biological activity of the GPA protein is altered. For example, glycosylation sites may be altered or removed.

Similarly, the biological function may be altered; for example, in some instances it may be desirable to have more or less potent granulopoietic activity.

The GPA proteins and nucleic acids of the invention can be made in a number of ways. As will be appreciated by those in the art, it is possible to synthesize proteins using standard techniques well known in the art. See for example Wilken et al., Curr. Opin. Biotechnol. 9:412–26 (1998), hereby expressly incorporated by reference.

Alternatively, and preferably, the proteins and nucleic acids of the invention are made using recombinant techniques. Using the nucleic acids of the present invention which encode a GPA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the GPA protein. The term "control sequences" refers to DNA sequences necessary for the expression of an operably linked coding sequence in a particular host organism.

The control sequences that are suitable for prokaryotes, for example, include a promoter, optionally an operator sequence, and a ribosome binding site. Eukaryotc cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The GPA nucleic acids are introduced into the cells. By "introduced into " or grammatical equivalents herein is meant that the nucleic acids enter the cells in a manner suitable for subsequent expression of the nucleic acid. The method of introduction is largely dictated by the targeted cell type, discussed below. Exemplary methods include $CaPO_4$ precipitation, liposome fusion, lipofectin®, electroporation, viral infection, etc. The GPA nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The GPA proteins of the present invention are produced by culturing a host cell transformed with an expression vector containing nucleic acid encoding a GPA protein, under the appropriate conditions to induce or cause expression of the GPA protein. The conditions appropriate for GPA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, *Pichia Pastoris*, etc.

In a preferred embodiment, the GPA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenyltion signals include those derived form SV40.

In a preferred embodiment, when combinations of variable positions are to be made, the nucleic acids encoding the GPA proteins are made using a variety of combinatorial techniques. For example, "shuffling" techniques such as are outlined in U.S. Pat. Nos. 5,811,238; 5,605,721 and 5,830,721, and related patents, all of which are hereby expressly incorporated by reference.

In a preferred embodiment, multiple PCR reactions with pooled oligonucleotides is done, as is generally depicted in FIG. 12. In this embodiment, overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of variable positions.

In a preferred embodiment, the different oligonucleotides are added in relative amounts corresponding to a probability distribution table; that is, as shown in FIGS. 3–10, different amino acids have different probabalistic chances of being at a particular position. Thus, for example, as shown in FIG. 4, out of the top 1000 sequences, position 103 has valine 35% of the time, leucine 26% of the time, and isoleucine 31% of the time. The multiple PCR reactions thus result in full length sequences with the desired combinations of variable amino acids in the desired proportions.

The total number of oligonucleotides needed is a function of the number of positions being mutated and the number of mutations being considered at these positions:

(number of oligos for constant positions)+M1+M2+M3+...
Mn=(total number of oligos required)

where Mn is the number of amino acids considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being varied, or for more than one position being varied. The multiple positions being varied must be close in sequence to prevent the oligo length from being impractical. For multiple variable positions on an oligonucleotide, particular combinations of variable residues can be included or excluded in the library by including or excluding the oligonucleotide encoding that combination. The total number of oligonucleotides required increases when multiple variable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for insertions or deletions can result in secondary libraries defining different length proteins, which can be expressed by a library of pooled oligonucleotide of different lengths.

In a preferred embodiment, error-prone PCR is done. See U.S. Pat. Nos. 5,605,793, 5,811,238, and 5,830,721, all of which are hereby incorporated by reference. This can be done on the optimal sequence or on top members of the GPA set. In this embodiment, the gene for the optimal GPA sequence found in the computational screen can be synthesized. Error prone PCR is then performed on the optimal sequence gene in the presence of oligonucleotides that code for the variable residues at the variant positions (bias oligonucleotides). The addition of the oligonucleotides will create a bias favoring the incorporation of the variations in the secondary library. Alternatively, only oligonucleotides for certain variations may be used to bias the library.

In a preferred embodiment, error-prone PCR in combination with the overlapping oligonucleotide method outlined in FIG. 12 is done.

In a preferred embodiment, gene shuffling with error prone PCR can be performed on the gene for the optimal sequence, in the presence of bias oligonucleotides, to create a DNA sequence library that reflects the proportion of the variations. The choice of the bias oligonucleotides can be done in a variety of ways; they can chosen on the basis of their frequency, i.e. oligonucleotides encoding high variation frequency positions can be used; alternatively, oligonucleotides containing the most variable positions can be used, such that the diversity is increased; if the GPA protein set is ranked, some number of top scoring positions can be used to generate bias oligonucleotides; random positions may be chosen; a few top scoring and a few low scoring ones may be chosen; etc. What is important is to generate new sequences based on preferred variable positions and sequences. Similarly, a top set of GPA proteins may be "shuffled" using traditional shuffling methods or the overlapping oligonucleotide methods of FIG. 12.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the GPA nucleic acid.

In a preferred embodiment, the GPA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the GPA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the GPA protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histdine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, GPA proteins are produced in insect cells. Expression vectors for the transformation of insect cells, and in particular, baculovirus-based expression vectors, are well known in the art.

In a preferred embodiment, GPA protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the GPA polypeptides of the invention may be further fused to other proteins, if desired, for example to increase expression.

In one embodiment, the GPA nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the GPA proteins may be covalently modified. One type of covalent modification includes reacting targeted amino acid residues of an GPA polypeptide with an organic derivatizing agent that is capable of reacting with selected side chains or the N-or C-terminal residues of an GPA polypeptide. Derivatzation with bifunctional agents is useful, for instance, for crosslinking GPA to a water-insoluble support matrix or surface for use in the method for purifying anti-GPA antibodies or screening assays, as is more fully described below. Commonly used crosslinking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylabon of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidabon of any C-terminal carboxyl group.

Another type of covalent modification of the GPA polypeptide included within the scope of this invention comprises altering the native glycosylabon pattern of the polypeptide. "Altering the native glycosylation pattern" is intended for purposes herein to mean deleting one or more carbohydrate moieties found in native sequence GPA polypeptide, and/or adding one or more glycosylabon sites that are not present in the native sequence GPA polypeptide.

Addition of glycosylation sites to GPA polypeptides may be accomplished by altering the amino acid sequence thereof. The alteration may be made, for example, by the addition of, or substitution by, one or more serine or threonine residues to the native sequence GPA polypeptide (for O-linked glycosylation sites). The GPA amino acid sequence may optionally be altered through changes at the DNA level, particularly by mutating the DNA encoding the GPA polypeptide at preselected bases such that codons are generated that will translate into the desired amino acids. Another means of increasing the number of carbohydrate moieties on the GPA polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the GPA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of GPA comprises linking the GPA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

GPA polypeptides of the present invention may also be modified in a way to form chimeric molecules comprising an GPA polypeptide fused to another, heterologous polypeptide or amino acid sequence. In one embodiment, such a chimeric molecule comprises a fusion of an GPA polypeptide with a tag polypeptide which provides an epitope to which an anti-tag antibody can selectively bind. The epitope tag is generally placed at the amino-or carboxyl-terminus of the GPA polypeptide. The presence of such epitope-tagged forms of an GPA polypeptide can be detected using an antibody against the tag polypeptide. Also, provision of the epitope tag enables the GPA polypeptide to be readily purified by affinity purification using an anti-tag antibody or another type of affinity matrix that binds to the epitope tag. In an alternative embodiment, the chimeric molecule may comprise a fusion of an GPA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnoloqy*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [(Lutz-Freyermuth et al., *Proc. Natl. Acad. Sci. USA*, 87:6393–6397 (1990)].

In a preferred embodiment, the GPA protein is purified or isolated after expression. GPA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the GPA protein may be purified using a standard anti-library antibody column. Ultrafiltrabon and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the GPA protein. In some instances no purification will be necessary. A preferred method for purification is outlined in the examples.

Once made, the GPA proteins and nucleic acids of the invention find use in a number of applications.

In a preferred embodiment, the GPA proteins are administered to a patent to treat a G-CSF-associated disorder.

By "G-CSF associated disorder" or "neutropenic" or "G-CSF responsive disorder" or "condition" herein is meant a disorder that can be ameliorated by the administration of a compound with a GPA protein, including, but not limited to, neutropenia associated with cancer therapies including chemotherapy and radiation therapy; radiation accidents; bone marrow transplantation; bone marrow suppression conditions, for example those associated with AIDS; myelodysplastc syndromes characterized by granulocyte functional abnormalities; severe infections; etc. In addition, treatment with the GPA proteins of the invention can be used to enhance peripheral blood progenitor cell collection.

In a preferred embodiment, a therapeutically effective dose of a GPA protein is administered to a patient. By "therapeutcally effective dose" herein is meant a dose that produces the effects for which it is administered. The exact dose will depend on the purpose of the treatment, and will be ascertainable by one skilled in the art using known techniques. In a preferred embodiment, dosages of about 5 μg/kg are used, administered either intravenously or subcutaneously. As is known in the art, adjustments for GPA degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the GPA proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the GPA protein may be directly applied as a solution or spray.

The pharmaceutical compositions of the present invention comprise a GPA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutcally acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutcally acceptable base addition salts" include those derived from inorganic bases such as sodium, potassium, lithium, ammonium, calcium, magnesium, iron, zinc, copper, manganese, aluminum salts and the like.

Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, GPA proteins are administered as therapeutic agents, and can be formulated as outlined above. Similarly, GPA genes (including both the full-length sequence, partial sequences, or regulatory sequences of the GPA coding regions) can be administered in gene therapy applications, as is known in the art. These GPA genes can include antisense applications, either as gene therapy (i.e. for incorporation into the genome) or as antisense compositions, as will be appreciated by those in the art.

In a preferred embodiment, the nucleic acid encoding the GPA proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. U.S.A.*, 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfecton with viral (typically retroviral) vectors and viral coat protein-liposome mediated transfection [Dzau et al., *Trends in Biotechnology*, 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.*, 262:4429–4432 (1987); and Wagner et al., *Proc. Natl. Acad. Sci. U.S.A.*, 87:3410–3414 (1990). For review of gene marking and gene therapy protocols see Anderson et al., *Science*, 256:808–813 (1992).

In a preferred embodiment, GPA genes are administered as DNA vaccines, either single genes or combinations of GPA genes. Naked DNA vaccines are generally known in the art. Brower, Nature Biotechnology, 16:1304–1305 (1998). Methods for the use of genes as DNA vaccines are well known to one of ordinary skill in the art, and include placing a GPA gene or portion of a GPA gene under the control of a promoter for expression in a GPA patient. The GPA gene used for DNA vaccines can encode full-length GPA proteins, but more preferably encodes portions of the GPA proteins including peptides derived from the GPA protein. In a preferred embodiment a patient is immunized with a DNA vaccine comprising a plurality of nucleotide sequences derived from a GPA gene. Similarly, it is possible to immunize a patient with a plurality of GPA genes or portions thereof as defined herein. Without being bound by theory, expression of the polypeptide encoded by the DNA vaccine, cytotoxic T-cells, helper T-cells and antibodies are induced which recognize and destroy or eliminate cells expressing GPA proteins.

In a preferred embodiment, the DNA vaccines include a gene encoding an adjuvant molecule with the DNA vaccine. Such adjuvant molecules include cytokines that increase the immunogenic response to the GPA polypeptide encoded by the DNA vaccine. Additional or alternative adjuvants are known to those of ordinary skill in the art and find use in the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Design and Characterization of Novel GPA Proteins

Protein Design

Summary: Sequences for novel granulopoietic proteins (GPA proteins) were designed by simultaneously optimizing residues in the buried core of the protein using Protein Design Automation (PDA) as described in WO98/47089 and U.S. Ser. No. 09/127,926, both of which are expressly incorporated by reference in their entirety. Several core designs were completed, with 25–34 residues considered, corresponding to $10^{27}$–$10^{28}$ sequence possibilities. Residues unexposed to solvent were designed in order to minimize changes to the molecular surface and to limit the potential for antgenicity of designed novel protein analogues. Calculations required from 12–24 hours on 16 Silicon Graphics R10000 CPU's. The global optimum sequence from each design was selected for characterization. From 10–14 residues were changed from hG-CSF in the designed proteins, out of 174 residues total. Additional designs were done where 14–24 boundary positions were optimized resulting in 12–20 mutated residues. These designs were repeated using the optimal sequence obtained from one of the core designs as the template structure, again producing optimal sequences with from 12–20 mutations. Only the global optimum sequences were selected for experimental study because of the high stringency of PDA and the very low false positive rate.

Computational Protocols

Template structure preparation: The template structure was produced using homology modeling. The crystal structure of bovine G-CSF (PDB record 1 bgc) was used as the starting point for modeling since the crystal structure of human G-CSF is at lower resolution and is missing key fragments including a restraining disulfide bond between positions 64 and 74. Bovine G-CSF also serves as a good model for human G-CSF since the sequences are the same length and 142 out of 174 amino acids are identical (81%). The 32 residues that differ in the bovine sequence were replaced with the human residues for those positions and the conformations of the replaced side chains were optimized using PDA. The optimization was initially done on all the replaced residues except position 167; typical PDA parameters were used (the van der Waals scale factor was set to 0.9, the H-bond potential well-depth was set to 8.0 kcal/mol, and the solvation potential was calculated using type 2 solvation with a nonpolar burial energy of 0.048 kcal/mol and a nonpolar exposure multiplication factor of 1.6). For position 167, the Gly in bovine G-CSF was replaced with the human residue for this position (Val).

However, due to steric constraints between position 167 and the disulfide bond between positions 64 and 74, the Val at this position was optimized using less restrictive steric constraints (PDA was run using a van der Waals scale factor of 0.7 instead of the typical value of 0.9). The entire structure was then minimized for 50 steps using conjugate gradient minimization and the Dreiding II force field. This minimized structure was used as the template for all the designs.

Design strategies: Core residues were selected for design since optimization of these positions can improve stability, although stabilization has been obtained from modifications at other sites as well. Core designs also minimize changes to the molecular surface and thus limit the designed protein's potential for antigenicity. PDA calculations were run on three core designs; core3 had 34 core positions that were allowed to vary, core4 had 26, and core4v had 25 (see FIG. 2). The core3 variable positions were selected from the entire length of the helices, while core4 and core4v's variable positions were selected from the interior (not at the ends) of the helices. Only hydrophobic amino acids were allowed at the variable core positions. These included Ala, Val, Phe, Ile, Leu, Tyr and Trp. Gly was also allowed for the variable positions that had Gly in the bovine wild type structure (positions 28, 149, 150, and 167). Met and Pro were not allowed.

Two boundary designs were also done; bndry4_2 had 24 variable boundary residues, and bndry4_AD had 14 (see FIG. 2). The bndry4_AD design was restricted to boundary residues on the outer two helices (A and D) since initial calculations suggested that the most pronounced changes in helical propensity result from modifications at these locations, and we anticipated that improvements in helical propensity might lead to improved stability. Two additional boundary designs were done (bndry4_2_core4 and bndry4_AD_core4) which allowed the same boundary positions to vary but used the optimal sequence from the core4 design as the template. That is, these designs were required to keep the 10 core mutations (amino acid and conformation) that resulted from the core4 PDA calculations (see FIG. 3). The boundary designs allowed the following amino acids at the variable positions: Ala, Val, Leu, Ile, Asp, Asn, Glu, Gln, Lys, Ser, Thr, and Hsp (a protonated His). Met, Pro, Cys, Gly, Arg, and the aromatics Trp, Tyr, and Phe were not allowed.

PDA Calculations

The PDA calculations for all the designs were run using the a2h1p0 rotamer library. This library is based on the backbone-dependent rotamer library of Dunbrack and Karplus (Dunbrack and Karplus, 1993) but includes more rotamers for the aromatic and hydrophobic amino acids; $X_1$ and X2 angle values of rotamers for all the aromatic amino acids and $X_1$ angle values for all the other hydrophobic amino acids were expanded ±1 standard deviation about the mean value reported in the Dunbrack and Karplus library. Typical PDA parameters were used: the van der Waals scale factor was set to 0.9, the H-bond potential well-depth was set to 8.0 kcal/mol, the solvation potential was calculated using type 2 solvation with a nonpolar burial energy of 0.048 kcal/mol and a nonpolar exposure multiplication factor of 1.6, and the secondary structure scale factor was set to 0.0 (secondary structure propensities were not considered). Calculations required from 12–24 hours on 16 Silicon Graphics R10000 CPU's.

Optimal Sequences

The optimal sequence selected by PDA for each of the designs is shown in FIG. 3. In the core designs, from 10 to 14 residues were changed compared to wild type, while the boundary designs produced 20 mutations for bndry4_2 (all four helices designed) and 12 mutations for bndry4_AD (only A and D helices designed). Including the core4 mutants in the template resulted in the same number of boundary mutations (20 for bndry4_core4; 12 for bndry4_AD_core4), but different amino acids were selected at some of the mutated positions.

Monte Carlo Analysis

Monte Carlo analysis of the sequences produced by PDA shows the ground state (optimal) amino acid and amino acids allowed for each variable position and their frequencies of occurrence (see FIGS. 4 through 10).

Cloning and Expression

Summary: A gene for met hG-CSF was synthesized from partially overlapping oligonucleotides (approximately 100 bases) that were extended and PCR amplified; see FIG. 1B. Codon usage was optimized for *E. coli* and several restriction sites were incorporated to ease future cloning. These partial genes were cloned into a vector and transformed into *E. coli* for sequencing. Several of these gene fragments were then cloned into adjacent positions in an expression vector (pET17 or pET21) to form the full length gene for met hG-CSF (528 bases) and transformed into *E coli* for expression. Protein was expressed in *E. coli* in insoluble inclusion bodies (data not shown) and its identity was confirmed by immunoblot of SDS-PAGE using a commercial Mab against hG-CSF. A similar strategy was followed for all of the novel GPA proteins and all were expressed (data not shown).

Cloning

To clone the gene, pairs of partially complementary oligonucleotides were synthesized and annealed by heating to 70° C. for 10 min and cooling to room temperature. The overlapping oligonucleotides (100 mers) were extended using Klenow fragment for 1 hour at 37° C. These extended oligonucleotides were then used as templates for PCR with primers complementary to the terminal 20 nucleotides of each end. PCR products were cloned into the vector pCR-Blunt (Invitrogen) according to the manufacturer's recommendations, and transformed into Gibco-BRL Subcloning Efficiency *E. coli* DH5α cells. The DNAs from several colonies were isolated using a Qiagen Miniprep Spin Kit, and sequenced by an Applied Biosystems 377XL automated flourescent DNA sequencer.

Expression

To express the protein, sequenced genes were subcloned between the NdeI and XhoI sites of Novagen's pET21a (+) vector and transformed into *E. coli* BL21 (DE3) cells. Protein expression was induced by growing the *E. coli* cells in Circlegrow media (Bio 101) with shaking at 37° C. to a density of 0.5 $OD_{550}$. IPTG was then added to a final concentration of 1 mM, and growth was allowed to continue for a further 3 hours. The expressed protein incorporated a Met at the N-terminus; our numbering begins with the next residue, a Thr.

To confirm expression of the protein, 10 µl samples were removed prior to addition of IPTG and at the end of the three hour incubation. These samples were electrophoresed through a 15% SDS-polyacrylamide gel and stained with Coomassie blue R-250. Expression of protein with the expected molecular weight could readily be observed. Confirmation that the protein was GCSF was obtained by immunoblot analysis using monoclonal antibodies directed to either the N-terminal 20 amino acids or the C-terminal 18 amino acids (Santa Cruz Biotechnology).

Isolation and Purification

Summary: Protein was isolated by solubilizing the inclusion bodies in detergent and refolding the protein in the presence of $CuSO_4$ to promote formation of native disulfide bonds. The solubilized protein mixture was loaded onto a size exclusion column to separate monomeric protein from aggregates and contaminants from the preparation. Fractions containing monomeric met hG-CSF were collected and assessed for purity by reversed phase HPLC. Greater than 95% purity was confirmed. The designed GPA proteins eluted slightly later than wildtype met hG-CSF.

HPLC purification: The mixture was directly loaded onto the size exclusion column (10 mm×300 mm loaded with superdex prep 75 resin purchased from Pharmacia) and eluted at a flow rate of 0.8 ml/min using the column buffer (100 mM $Na_2SO_4$, 50 mM Tris, pH 7.5). The peaks are monitered by UV detector at dual wavelengths of 214 and 280 nm. Albumin, carbonic anhydrate, cytochrome C and aprotinin were used to calibrate the molecular size of proteins versus elution time. The monomeric peak that elutes around the expected elution time for each protein was collected and the buffer was exchanged into 10mM NaOAc at pH 4 for biophysical characterization. For long term storage, a buffer of 5% sorbitol, 0.004% Tween 80, and 10 mM NaOAc at pH 4 was used. The proteins were >98% pure as judged by reversed phase HPLC on a C4 column (3.9 mm×150 mm) with linear acetonitrile-water gradient containing 0.1% TFE.

Isolation and refolding from inclusion bodies: To isolate inclusion bodies, the *E. coli* cells were pelleted by centrifugation at 8000 rpm in a Beckman J2-17 rotor. The cells were re-suspended in 50 mM Tris.HCl pH8.0, 10 mM $MgCl_2$ at 5 mls per gram of pelleted cells. Lysozyme was added to a final concentration of 0.1 mg/ml, and the cells were incubated at 30° C. for 30 min. The cells were then rapidly frozen and thawed, and DNase 1 was added to a concentration of 10 μg/ml. After incubation at 37° C. for 30 minutes, the inclusion bodies were isolated by centrifugation at 12 000 rpm for 30 min and washed twice with 50 mM Tris.HCl pH8.0, 10 mM $MgCl_2$.

The protein precipitate was washed and fully solubilized in 2% sarkosyl, 50 mM Tris, pH 8.0. $CuSO_4$ was then added into the mixture to reach a concentration of 20 uM. The mixture was stirred for 8–10 hours to refold the proteins by forming disulfide bonds under air oxidation.

Spectroscopic Characterization

Summary: Protein structure was assessed by circular dichroism (CD). The CD spectra for met hG-CSF and the GPA proteins tested were nearly identical to each other and to published spectra of met hG-CSF. These spectra indicate highly similar secondary structure and tertiary folds for the GPA proteins and met hG-CSF. Thermal stability was assessed by monitoring the temperature dependence of the CD signal at 222 nm, a wavelength diagnostic for helical protein structure. The thermal stabilities of the proteins are shown in FIG. 13, with core4 approximately 10° C. more stable than met hG-CSF and core3 and core4v having very similar thermal stabilities to met hG-CSF. As in previously published PDA designed proteins, the origin of the increased stability likely results from an improved balance between packing interactions and hydrophobic burial of side chains. The thermal stabilities of three additional GPA proteins (sm0, fm3 and fm4) derived by reverting some of the core mutant positions to wild type are shown in FIG. 16.

Spectroscopic Characterization

The concentrations of the proteins were determined by UV spectroscopy at 280 nm using the extinction coefficients shown in FIG. 16. CD spectra were measured on an Aviv 202DS spectrometer equipped with a Peltier temperature control unit. The ellipticity was calibrated with (+)-10-camphorsulfonic acid. The thermal transition curves were recorded at 222 nm in a buffer of 10 mM NaOAc at pH 4.0 every 2.5° C. with an averaging time of 5 s and an equilibration time of 3 min. The melting temperature ($T_m$) value of each protein was derived from the derivative curve of the ellipticity at 222 nm vs. temperature. The $T_m$ values were reproducible to within 1° for the same protein at the concentrations used (~0.1 mg/ml). Thermal denaturation curves are shown in FIG. 13. The $T_m$'s for core4, core4v and core3 and three proteins derived from them (sm0, fm4 and fm7) are shown in FIG. 16.

In Vitro Biological Activity

Summary: FIG. 14 shows the dose response curves for met hG-CSF and three GPA proteins. Mouse leukocytes were transfected with human G-CSF receptor, making leukocyte proliferation dependent on G-CSF signaling activity via the G-CSF receptor. Leukocyte proliferation is measured by incorporation of brominated uracil (BrdU) measured by ELISA. GPA protein granulopoietic activity is measured by quantifying cell proliferation as a function of protein concentration. Two hG-CSF samples were also tested, one produced as described herein and a commercially available hG-CSF from R&D Systems. Dose response curves were very similar for all of the proteins tested, except for core4, which showed approximately two times the potency of met hG-CSF. FIG. 15 shows the appearance of a typical 96 well plate ELISA of control samples with met hG-CSF. The statistical analysis of the dose response assay (8 replicates) shows that core4 was highly significantly more potent than the other GPA proteins and met hG-CSF. The origin of this effect is unclear, and could be from increased affinity for the receptor, increased stability of core4 under cell culture assay conditions, or a combination.

Cell culture: The cells used in the proliferation assay were Ba/F3 (murine lymphoid) cells stably transfected with the gene encoding the human Class 1 GCSF receptor (a kind gift from Dr. Belinda Avalos, Ohio State University). These cells were maintained in RPM1 medium 1640 (Gibco-BRL) at 5% $CO_2$, 37° C. in high humidity. They were passaged every 2–3 days by a 1 in 10 dilution into fresh media.

Cell proliferation assay: Cell proliferation in response to GCSF was detected by 5-bromo-2'-deoxyuridine (BrdU) incorporation quantified by a BrdU-specific ELISA kit as described by the manufacturer (Boehringer Mannheim). Briefly, $1\times10^5$ to $1\times10^6$ Ba/F3 cells/ml are incubated with varying amounts of GCSF ($1\times10^2$ pg/ml to $1\times10^5$ pg/ml) for 42 hrs before the addition of 10 $\mu$M BrdU. After further incubation of 22 hrs, the cells are lysed and the DNA denatured using FixDenat (Boehringer Mannheim). Incorporation of BrdU into DNA was then quantified with an ELISA that utilizes a peroxidase-conjugated monoclonal antibody against BrdU. Peroxidase activity was measured at 450 nm by a BioRad Model 550 microtitre plate reader. Typically, each experiment contained 8 replicates spread over 4 plates. Data was analyzed by Kaleidagraph (Synergy Software) and Statistica (Statsoft).

Storage Stability

The storage stability of core4 was assessed by incubation at both 37 and 50° C. under solution conditions identical in composition to that used in the commercial formulation of Neupogen. Accelerated degradation was followed by observing the disappearance of monomeric protein with size exclusion chromatography, since aggregation is the predominant mechanism of inactivation of G-CSF. Even under optimized formulation conditions, core4 is significantly more stable than met hG-CSF (FIG. 15).

We claim:

1. A non-naturally occurring GPA protein comprising at least five amino acid substitutions as compared to hG-CSF protein, wherein at least five of said substitutions are selected from the amino acid residues at positions selected from 14, 17, 20, 21, 24, 27, 28, 31, 32, 34, 35, 38, 78, 79, 85, 89, 91, 92, 99, 102, 103, 107, 109, 110, 113, 116, 120, 145, 146, 147, 148, 151, 153, 155, 156, 157, 160, 161, 163, 164, 167, 168 and 170.

2. A non-naturally occurring GPA protein according to claim 1 wherein said GPA protein has at least 10 amino acid substitutions.

3. A non-naturally occurring GPA protein according to claim 2 wherein 10 of said substitutions are at positions 17, 28, 78, 85, 103, 110, 113, 151, 153 and 168.

4. A non-naturally occurring GPA protein according to claim 3 wherein said substitutions are 17L, 28A, 78F, 85F, 103V, 110I, 113L, 151I, 153I and 168F (SEQ ID NO: 7).

5. A non-naturally occurring GPA protein according to claim 1, wherein at least five of said substitutions are selected from the amino acid residues at positions selected from 14, 20, 27, 32, 34, 38, 79, 91, 102, 107, 109, 116, 120, 146, 147, 148, 155, 156 and 163.

6. A GPA protein according to claim 5 wherein said substitutions are 14I, 20L, 27E, 32L, 34E, 38H, 79L, 91K, 102K, 107I, 109E, 116I, 120L, 146K, 147E, 148D, 155I, 156L and 163A, (SEQ ID NO: 18).

7. A recombinant nucleic acid encoding the non-naturally occurring GPA protein of claim 1.

8. An expression vector comprising the recombinant nucleic acid of claim 7.

9. A host cell comprising the expression vector of claim 8.

10. A host cell comprising the recombinant nucleic acid of claim 1.

11. A method of producing a non-naturally occurring GPA protein comprising culturing the host cell of claim 10 under conditions suitable for expression of said nucleic acid.

12. The method according to claim 11 further comprising recovering said GPA protein.

13. A pharmaceutical composition comprising a GPA protein according to claim 1 and a pharmaceutical carrier.

14. A non-naturally occurring GPA protein according to claim 1, wherein at least five of said substitutions comprises substitutions at positions selected from 14, 17, 20, 27, 28, 32, 34, 35, 38, 78, 79, 85, 89, 9, 92, 102, 103, 107, 109, 110, 113, 116, 120, 146, 147, 148, 151, 153, 155, 156, 164, 167, and 168.

15. A non-naturally occurring GPA protein according to claim 14 wherein said substitutions are 14I, 17L, 20L, 27E, 28A, 32L, 34E, 38H, 78F, 79L, 85F, 91K, 102K, 103V, 107I, 109E, 110I, 113L, 116I, 120L, 146K, 147E, 148D, 151I, 153I, 155I, 156L, 164A and 168F (SEQ ID NO: 4).

16. A non-naturally occurring GPA protein according to claim 14 wherein said substitutions are 17L, 28A, 35I, 78F, 85F, 89F, 92F, 113L, 151I, 153I, and 168F (SEQ ID NO: 9).

17. A non-naturally occurring GPA protein according to claim 14 wherein said substitutions are 17L, 21I, 28A, 78F, 85F, 110I, 113L, 151I, 153I, 157I, 160W, 161F, 167A, and 168F (SEQ ID NO: 8).

18. A non-naturally occurring GPA protein according to claim 14 wherein said substitutions are 17L, 28A, 78F, 85F, 113L, 151I, 153I, and 168F (SEQ ID NO. 14).

19. A non-naturally occurring GPA protein comprising the amino acid sequence of SEQ ID NO: 10.

20. A non-naturally occurring GPA polypeptide comprising the amino acid sequence of SEQ ID NO: 11.

21. A non-naturally occurring GPA protein comprising at least five amino acid substitutions as compared to hG-CSF protein, wherein at least five of said substitutions are selected from the amino acid residues at positions selected from 17L, 17I; 21V, 21I: 24V, 24I; 28A, 28L; 31V, 31L; 78F; 85F, 85Y; 89L, 89F; 103V, 103L, 103I; 110V, 110L, 110I; 113L; 151I; 153V, 153I; 157L, 157I; 160F, 160W; 161L, 161F; and 168F.

22. A non-naturally occurring GPA protein comprising at least five amino acid substitutions as compared to hG-CSF protein, wherein at least five of said substitutions are selected from the group consisting of 17L, 17V, 17I, 21V, 21I, 21F; 24I, 24V; 28A, 28L; 31L, 31A, 31V, 31I; 78F, 78V; 82L, 82F; 85F, 85V, 85I, 85Y; 89L, 89F, 89W; 103V, 103A, 103L, 103I; 106L, 106V; 110I, 110V, 110L; 113L; 151I, 153I, 153V; 157L, 157V, 157I; 160F, 160W; 161L, 161F; 167A; and 168F.

23. A non-naturally occurring GPA protein comprising at least five amino acid substitutions as compared to hG-CSF protein, wherein at least five of said substitutions are selected from the group consisting of 17L, 17V, 17I; 21V, 21A, 21I, 21F, 21Y; 24I, 24A, 24V, 24L; 28A, 28L; 31L, 31V; 35I, 35V; 78F, 78A, 78V, 78L, 78I, 78Y; 82L, 82A, 82F; 85F, 85W; 89F, 89L, 89W; 92F; 103L; 103L, 103I; 106L, 106V; 110V, 110A, 110L, 110I; 113L, 113A, 113F; 117I, 117A, 117V, 117L, 117F, 117W; 151I, 153I; 157L, 157A, 157V, 157I; 160F, 160W; 161L, 161A, 161V, 161F; and 168F.

24. A non-naturally occurring GPA protein comprising at least five amino acid substitutions as compared to hG-CSF protein, wherein at least five of said substitutions are selected from the group consisting of 14I; 20L; 27E; 32I; 34K, 34I, 34F; 38V, 38I, 38E, 38K; 79L; 91K; 99V, 99L; 102L, 102I; 107I; 109E, 109V; 116I, 116L, 116K; 120L; 145Q, 145E; 146K, 146Q; 147E; 148T, 148A, 148D; 155I; 156L; 164A; 170H, 170L, 170E, and 170Q.

25. A non-naturally occurring OPA protein comprising at least five amino acid substitutions as compared to hG-CSF protein, wherein at least five of said substitutions are selected from the group consisting of 14I, 14L; 20L; 27E, 27S; 32L, 32V, 32I; 34E, 34Q, 34K; 38H, 38V, 38I, 38E, 38K; 79L; 91K; 99L, 99E; 102K, 102T, 102V, 102L, 102I, 102E, 102Q; 107I, 107V, 107L; 109E, 109V, 109D, 109Q; 116I, 116V, 116L, 116E, 116K; 120L; 145Q, 145E; 146L, 146Q; 147E, 147K; 148D, 148A, 148T; 155I; 156L; 164A; 170?, 170D, 170L, 170E, 170Q, and 170K.

26. A non-naturally occurring GPA protein comprising at least five amino acid substitutions as compared to hG-CSF protein, wherein at least five of said substitutions arc selected from the group consisting of 14I, 14L; 20L; 27E; 32T; 34E, 34I, 34Q, 34K; 38V, 38I, 38H, 38E, 38K; 145Q, 145E; 146L, 146Q; 147E; 148T, 148A, 148D; 155I; 156L; 164A; 170H, 170D, 170L, 170E, 170Q, and 170K.

27. A non-naturally occurring GPA protein comprising at least five amino acid substitutions as compared to hG-CSF protein, wherein at least five of said substitutions arc selected from the group consisting of 14I, 14L; 20L; 27E; 32L, 32V, 32I; 34E, 34Q, 34K; 38V, 38I, 38H, 38E, 38K; 145Q, 145E; 146L, 146Q; 147E; 148D, 148A, 148T; 155I; 156L; 164S; 170H, 170L, 170E, and 170Q.

* * * * *

UNITED STATES PATENT AND TRADEMARK OFFICE
CERTIFICATE OF CORRECTION

PATENT NO. : 6,627,186 B1
DATED : September 30, 2003
INVENTOR(S) : Bassil I. Dahiyat and Peizhi Luo It is certified that error appears in the above-identified patent and that said Letters Patent is hereby corrected as shown below:

Column 53,
Line 8, delete "163".
Line 23, change "163" to -- 164 --.

Signed and Sealed this

Twenty-fourth Day of August, 2004

JON W. DUDAS
*Director of the United States Patent and Trademark Office*

```
                         SEQUENCE LISTING

<160> NUMBER OF SEQ ID NOS: 18

<210> SEQ ID NO 1
<211> LENGTH: 526
<212> TYPE: DNA
<213> ORGANISM: Homo sapiens

<400> SEQUENCE: 1
atgactccat taggtccagc ttcctctctg ccgcaaagct tcctgctgaa atgcctggaa      60
caggttcgta aaatccaggg tgatggtgct gctctgcagg aaaaactgtg cgctacctac     120
aaactgtgcc atccggaaga actggttctg ctgggtcact ccctgggtat cccgtgggcg     180
ccgctgagct cctgcccgag ccaggctctg cagctggctg gttgcctgtc caattgcac      240 agcggccttt tcctgtacca gggtctgctg caagctctgg aaggtactcc ccggaactgg     300
gtccgaccct ggacactctg cagctggacg tcgctgactt cgctaccacc atctggcagc     360
agatggaaga actgggtatg gctccggctc tgcagccgac ccagggtgct atgccggctt     420
tcgttccgct ttccagcgtc gcgcaggtgg cgttctggtt gctagccacc tgcagagctt     480
cctggaagtt tcctaccgtg ttctgcgtca cctggctcag ccgtga                    526

<210> SEQ ID NO 2
<211> LENGTH: 174
<212> TYPE: PRT
<213> ORGANISM: Homo sapiens

<400> SEQUENCE: 2

Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45
```

```
Leu Leu Gly His Ser Leu Gly Ile Pro Trp Ala Pro Leu Ser Ser Cys
    50              55                  60

Pro Ser Gln Ala Leu Gln Leu Ala Gly Cys Leu Ser Gln Leu His Ser
65              70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 3
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 3

```
Met Thr Pro Leu Gly Pro Ala Ser Ser Leu Pro Gln Ser Phe Ile Leu
-1  1               5                   10                  15

Lys Cys Leu Glu Leu Val Arg Lys Ile Gln Gly Glu Gly Ala Ala Leu
                20                  25                  30

Ile Glu Ile Leu Cys Ala Lys Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu Leu
65                  70                  75

Ser Gly Leu Phe Leu Tyr Gln Gly Leu Leu Gln Lys Leu Glu Gly Ile
80                  85                  90                  95

Ser Pro Glu Val Gly Pro Ile Leu Asp Thr Leu Ile Leu Glu Val Ala
                100                 105                 110

Asp Phe Ala Thr Ile Ile Trp Gln Leu Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Lys Glu Asp Gly Gly Val Leu Val Ala Ile Leu Leu Gln Ser
            145                 150                 155

Phe Leu Glu Val Ala Tyr Arg Val Leu Arg His Leu Ala Gln Pro
160                 165                 170
```

<210> SEQ ID NO 4
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide

```
<222> LOCATION: (2)..()

<400> SEQUENCE: 4

Met Thr Pro Leu Gly Pro Ala Ser Ser Leu Pro Gln Ser Phe Ile Leu
 -1   1               5                  10                  15

Lys Leu Leu Glu Leu Val Arg Lys Ile Gln Gly Glu Ala Ala Ala Leu
                 20                  25                  30

Leu Glu Glu Leu Cys Ala His Tyr Lys Leu Cys His Pro Glu Glu Leu
                 35                  40                  45

Val Leu Leu Gly His Ser Leu Gly Ile Pro Trp Ala Pro Leu Ser Ser
             50                  55                  60

Cys Pro Ser Gln Ala Leu Gln Leu Ala Gly Cys Leu Ser Gln Phe Leu
         65                  70                  75

Ser Gly Leu Phe Leu Phe Gln Gly Leu Leu Gln Lys Leu Glu Gly Ile
 80                  85                  90                  95

Ser Pro Glu Leu Gly Pro Lys Val Asp Thr Leu Ile Leu Glu Ile Ala
                100                 105                 110

Asp Leu Ala Thr Ile Ile Trp Gln Leu Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Lys Glu Asp Gly Gly Ile Leu Ile Ala Ile Leu Leu Gln Ser
        145                 150                 155

Phe Leu Glu Val Ala Tyr Arg Val Phe Arg His Leu Ala Gln Pro
160                 165                 170

<210> SEQ ID NO 5
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 5

Met Thr Pro Leu Gly Pro Ala Ser Ser Leu Pro Gln Ser Phe Ile Leu
 -1   1               5                  10                  15

Lys Cys Leu Glu Leu Val Arg Lys Ile Gln Gly Glu Gly Ala Ala Leu
                 20                  25                  30

Ile Glu Glu Leu Cys Ala His Tyr Lys Leu Cys His Pro Glu Glu Leu
                 35                  40                  45

Val Leu Leu Gly His Ser Leu Gly Ile Pro Trp Ala Pro Leu Ser Ser
             50                  55                  60

Cys Pro Ser Gln Ala Leu Gln Leu Ala Gly Cys Leu Ser Gln Leu His
         65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Lys Glu Thr Gly Gly Val Leu Val Ala Ile Leu Leu Gln Ser
        145                 150                 155
```

Phe Leu Glu Val Ala Tyr Arg Val Leu Arg His Leu Ala Gln Pro
160                 165                 170

<210> SEQ ID NO 6
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 6

Met Thr Pro Leu Gly Pro Ala Ser Ser Leu Pro Gln Ser Phe Ile Leu
-1  1               5                  10                  15

Lys Leu Leu Glu Leu Val Arg Lys Ile Gln Gly Glu Ala Ala Leu
                20                  25                  30

Leu Glu Glu Leu Cys Ala His Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Phe His
65                  70                  75

Ser Gly Leu Phe Leu Phe Gln Gly Leu Leu Gln Ala Leu Glu Gly Ile
80                  85                  90                  95

Ser Pro Glu Leu Gly Pro Thr Val Asp Thr Leu Gln Leu Asp Ile Ala
                100                 105                 110

Asp Leu Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Lys Glu Asp Gly Gly Ile Leu Ile Ala Ile Leu Leu Gln Ser
                145                 150                 155

Phe Leu Glu Val Ala Tyr Arg Val Phe Arg His Leu Ala Gln Pro
160                 165                 170

<210> SEQ ID NO 7
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 7

Met Thr Pro Leu Gly Pro Ala Ser Ser Leu Pro Gln Ser Phe Leu Leu
-1  1               5                  10                  15

Lys Leu Leu Glu Gln Val Arg Lys Ile Gln Gly Asp Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Phe His
65                  70                  75

Ser Gly Leu Phe Leu Phe Gln Gly Leu Leu Gln Ala Leu Glu Gly Ile

```
80                 85                 90                 95
Ser Pro Glu Leu Gly Pro Thr Val Asp Thr Leu Gln Leu Asp Ile Ala
                100                 105                110

Asp Leu Ala Thr Thr Ile Trp Gln Gln Met Glu Glu Leu Gly Met Ala
                115                 120                125

Pro Ala Leu Gln Pro Thr Gln Gly Ala Met Pro Ala Phe Ala Ser Ala
                130                 135                140

Phe Gln Arg Arg Ala Gly Gly Ile Leu Ile Ala Ser His Leu Gln Ser
            145                 150                 155

Phe Leu Glu Val Ser Tyr Arg Val Phe Arg His Leu Ala Gln Pro
160                 165                 170

<210> SEQ ID NO 8
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 8

Met Thr Pro Leu Gly Pro Ala Ser Ser Leu Pro Gln Ser Phe Leu Leu
-1  1               5                   10                  15

Lys Leu Glu Gln Ile Arg Lys Ile Gln Gly Asp Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Phe His
65                  70                  75

Ser Gly Leu Phe Leu Phe Gln Gly Leu Leu Gln Ala Leu Glu Gly Ile
80                  85                  90                  95

Ser Pro Glu Leu Gly Pro Thr Leu Asp Thr Leu Gln Leu Asp Ile Ala
                100                 105                110

Asp Leu Ala Thr Thr Ile Trp Gln Gln Met Glu Glu Leu Gly Met Ala
                115                 120                125

Pro Ala Leu Gln Pro Thr Gln Gly Ala Met Pro Ala Phe Ala Ser Ala
                130                 135                140

Phe Gln Arg Arg Ala Gly Gly Ile Leu Ile Ala Ser His Ile Gln Ser
            145                 150                 155

Trp Phe Glu Val Ser Tyr Arg Ala Phe Arg His Leu Ala Gln Pro
160                 165                 170

<210> SEQ ID NO 9
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 9

Met Thr Pro Leu Gly Pro Ala Ser Ser Leu Pro Gln Ser Phe Leu Leu
-1  1               5                   10                  15
```

-continued

```
Lys Leu Glu Gln Val Arg Lys Ile Gln Gly Asp Ala Ala Leu
            20                  25                  30

Gln Glu Lys Ile Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Phe His
65                  70                  75

Ser Gly Leu Phe Leu Phe Gln Gly Leu Phe Gln Ala Phe Glu Gly Ile
80                  85                  90                  95

Ser Pro Glu Leu Gly Pro Thr Leu Asp Thr Leu Gln Leu Asp Val Ala
            100                 105                 110

Asp Leu Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Ile Leu Ile Ala Ser His Leu Gln Ser
            145                 150                 155

Phe Leu Glu Val Ser Tyr Arg Val Phe Arg His Leu Ala Gln Pro
160                 165                 170
```

```
<210> SEQ ID NO 10
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 10
```

```
Met Thr Pro Leu Gly Pro Ala Ser Ser Leu Pro Gln Ser Phe Leu Leu
-1  1               5                   10                  15

Lys Ala Leu Glu Gln Val Arg Lys Ile Gln Gly Asp Ala Ala Ala Leu
            20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
            145                 150                 155

Phe Leu Glu Val Ser Tyr Arg Val Leu Arg His Leu Ala Gln Pro
160                 165                 170
```

```
<210> SEQ ID NO 11
<211> LENGTH: 175
```

```
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 11
```

Met Thr Pro Leu Gly Pro Ala Ser Ser Leu Pro Gln Ser Phe Leu Leu
-1  1           5                   10                  15

Lys Ala Leu Glu Gln Val Arg Lys Ile Gln Gly Asp Ala Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
    65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Ile Leu Ile Ala Ser His Leu Gln Ser
    145                 150                 155

Phe Leu Glu Val Ser Tyr Arg Val Leu Arg His Leu Ala Gln Pro
160                 165                 170

```
<210> SEQ ID NO 12
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 12
```

Met Thr Pro Leu Gly Pro Ala Ser Ser Leu Pro Gln Ser Phe Leu Leu
-1  1           5                   10                  15

Lys Leu Leu Glu Gln Val Arg Lys Ile Gln Gly Asp Ala Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Phe His
    65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Leu Ala Thr Thr Ile Trp Gln Gln Met Glu Glu Leu Gly Met Ala
            115                 120                 125

```
Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
        145                 150                 155

Phe Leu Glu Val Ser Tyr Arg Val Phe Arg His Leu Ala Gln Pro
160                 165                 170

<210> SEQ ID NO 13
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 13

Met Thr Pro Leu Gly Pro Ala Ser Ser Leu Pro Gln Ser Phe Leu Leu
 -1   1              5                  10                  15

Lys Leu Leu Glu Gln Val Arg Lys Ile Gln Gly Asp Ala Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
     50                  55                  60

Cys Pro Ser Gln Ala Leu Gln Leu Ala Gly Cys Leu Ser Gln Phe His
 65                  70                  75

Ser Gly Leu Phe Leu Tyr Gln Gly Leu Leu Gln Ala Leu Glu Gly Ile
 80                  85                  90                  95

Ser Pro Glu Leu Gly Pro Thr Leu Asp Thr Leu Gln Leu Asp Val Ala
                100                 105                 110

Asp Leu Ala Thr Thr Ile Trp Gln Gln Met Glu Glu Leu Gly Met Ala
             115                 120                 125

Pro Ala Leu Gln Pro Thr Gln Gly Ala Met Pro Ala Phe Ala Ser Ala
         130                 135                 140

Phe Gln Arg Arg Ala Gly Gly Ile Leu Ile Ala Ser His Leu Gln Ser
         145                 150                 155

Phe Leu Glu Val Ser Tyr Arg Val Phe Arg His Leu Ala Gln Pro
160                 165                 170

<210> SEQ ID NO 14
<211> LENGTH: 175
<212> TYPE: PRT
<213> ORGANISM: Artificial sequence
<220> FEATURE:
<223> OTHER INFORMATION: synthetic
<220> FEATURE:
<221> NAME/KEY: mat_peptide
<222> LOCATION: (2)..()

<400> SEQUENCE: 14

Met Thr Pro Leu Gly Pro Ala Ser Ser Leu Pro Gln Ser Phe Leu Leu
 -1   1              5                  10                  15

Lys Leu Leu Glu Gln Val Arg Lys Ile Gln Gly Asp Ala Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
```

```
            50                   55                  60
Cys Pro Ser Gln Ala Leu Gln Leu Ala Gly Cys Leu Ser Gln Phe His
    65                  70                  75

Ser Gly Leu Phe Leu Phe Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Leu Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Ile Leu Ile Ala Ser His Leu Gln Ser
    145                 150                 155

Phe Leu Glu Val Ser Tyr Arg Val Phe Arg His Leu Ala Gln Pro
160                 165                 170
```

<210> SEQ ID NO 15
<211> LENGTH: 175
<212> TYPE: PRT
<213> ORGANISM: Homo sapiens
<220> FEATURE:
<221> NAME/KEY: mat_peptide
<222> LOCATION: (2)..()

<400> SEQUENCE: 15

```
Met Thr Pro Leu Gly Pro Ala Ser Ser Leu Pro Gln Ser Phe Leu Leu
-1  1               5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
    65                  70                  75

Ser Gly Leu Phe Leu Tyr Gln Gly Leu Leu Gln Ala Leu Glu Gly Ile
80                  85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
    145                 150                 155

Phe Leu Glu Val Ser Tyr Arg Val Leu Arg His Leu Ala Gln Pro
160                 165                 170
```

<210> SEQ ID NO 16
<211> LENGTH: 528
<212> TYPE: DNA
<213> ORGANISM: Artificial sequence
<220> FEATURE:
<223> OTHER INFORMATION: synthetic

<400> SEQUENCE: 16
atgactccat taggtccagc ttcctctctg ccgcaaagct tcctgctgaa actgctggaa    60

-continued

```
caggttcgta aaatccaggg tgatgcagct gctctgcagg aaaaaatctg cgctacctac      120
aaactgtgcc atccggaaga actggttctg ctgggtcact ccctgggtat cccgtgggcg      180
ccgctgagct cctgcccgag ccaggctctg cagctggctg gttgcctgtc ccaattccac      240
agcggccttt tcctgttcca gggtctgttc caggctttcg aaggtatctc cccggaactg      300
ggtccgaccc tggacactct gcagctggac gtcgctgacc tggctaccac catctggcag      360
cagatggaag aactgggtat ggctccggct ctgcagccga cccagggtgc tatgccggct      420
ttcgcttccc ctttccagcg tcgcgcaggt ggcatcctga tcgctagcca cctgcagagc      480
ttcctggaag tttcctaccg tgttttccgt cacctggctc agccgtga                  528
```

<210> SEQ ID NO 17
<211> LENGTH: 528
<212> TYPE: DNA
<213> ORGANISM: Artificial sequence
<220> FEATURE:
<223> OTHER INFORMATION: synthetic

<400> SEQUENCE: 17

```
atgactccat taggtccagc ttcctctctg ccgcaaagct tcctgctgaa actgctggaa       60
caggttcgta aatccaggg tgatgcagct gctctgcagg aaaaactgtg cgctacctac      120
aaactgtgcc atccggaaga actggttctg ctgggtcact ccctgggtat cccgtgggcg      180
ccgctgagct cctgcccgag ccaggctctg cagctggctg gttgcctgtc ccaattccac      240
agcggccttt tcctgttcca gggtctgctg caagctctgg aagtatctc cccggaactg      300 ggtccgaccg ttgacactct gcagctggac atcgctgacc tggctaccac catctggcag      360
cagatggaag aactgggtat ggctccggct ctgcagccga cccagggtgc tatgccggct      420
ttcgcttccg ctttccagcg tcgcgcaggt ggcatcctga tcgctagcca cctgcagagc      480
ttcctggaag tttcctaccg tgttttccgt cacctggctc agccgtga                  528
```

<210> SEQ ID NO 18
<211> LENGTH: 528
<212> TYPE: DNA
<213> ORGANISM: Artificial sequence
220> FEATURE:
<223> OTHER INFORMATION: synthetic

<400> SEQUENCE: 18

```
atgactccat taggtccagc ttcctctctg ccgcaaagct tcctgctgaa actgctggaa       60
cagatccgta aaatccaggg tgatgcagct gctctgcagg aaaaactgtg cgctacctac      120
aaactgtgcc atccggaaga actggttctg ctgggtcact ccctgggtat cccgtgggcg      180
ccgctgagct cctgcccgag ccaggctctg cagctggctg gttgcctgtc ccaattccac      240
agcggccttt tcctgttcca gggtctgctg caagctctgg aagtatctc cccggaactg      300 ggtccgaccc tggacactct gcagctggac atcgctgacc tggctaccac catctggcag      360
cagatggaag aactgggtat ggctccggct ctgcagccga cccagggtgc tatgccggct      420
ttcgcttccg ctttccagcg tcgcgcaggt ggcatcctga tcgctagcca catccagagc      480
tggttcgaag tttcctaccg tgctttccgt cacctggctc agccgtga                  528
```